(12) United States Patent
Duke et al.

(10) Patent No.: US 10,297,350 B2
(45) Date of Patent: May 21, 2019

(54) RISK-BASED CONTROL-TO-RANGE

(71) Applicant: Roche Diabetes Care, Inc., Indianapolis, IN (US)

(72) Inventors: David L. Duke, Fishers, IN (US); Christian Ringemann, Mannheim (DE); Chinmay Uday Manohar, Fishers, IN (US); Alan Greenburg, Indianapolis, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 205 days.

(21) Appl. No.: 15/170,468

(22) Filed: Jun. 1, 2016

(65) Prior Publication Data

US 2017/0348484 A1 Dec. 7, 2017

(51) Int. Cl.
*G01N 33/48* (2006.01)
*G16H 50/20* (2018.01)
*G16H 50/30* (2018.01)
*G06F 19/00* (2018.01)
*A61B 5/145* (2006.01)
(Continued)

(52) U.S. Cl.
CPC ......... *G16H 50/20* (2018.01); *A61B 5/14532* (2013.01); *A61M 5/14244* (2013.01); *A61M 5/1723* (2013.01); *G06F 19/00* (2013.01); *G06F 19/3468* (2013.01); *G16H 50/30* (2018.01); *A61M 2005/14208* (2013.01); *A61M 2205/35* (2013.01); *A61M 2205/3569* (2013.01); *A61M 2205/3584* (2013.01); *A61M 2205/50* (2013.01);
(Continued)

(58) Field of Classification Search
None
See application file for complete search history.

(56) References Cited

U.S. PATENT DOCUMENTS

| 6,572,545 | B2 | 6/2003 | Knobbe et al. |
| 6,575,905 | B2 | 6/2003 | Knobbe et al. |

(Continued)

FOREIGN PATENT DOCUMENTS

| EP | 2762073 A1 | 8/2014 |
| WO | 2002/24065 A1 | 3/2002 |

(Continued)

OTHER PUBLICATIONS

International Search Report pertaining to PCT application No. PCT/US2017/031661, filed May 9, 2017, 6 pages.

(Continued)

*Primary Examiner* — Larry D Riggs, II
(74) *Attorney, Agent, or Firm* — Dinsmore & Shohl, LLP

(57) ABSTRACT

Methods and systems are disclosed for determining a basal rate adjustment of insulin based on risk associated with a glucose state of a person with diabetes. A method may include detecting a glucose state of the person based on a received glucose measurement signal and determining a current risk metric associated with the detected glucose state. The method may include determining a current risk metric associated with the detected glucose state based on a weighted average of cumulative hazard values of return paths generated from a glucose state distribution around a detected glucose state. The method may include calculating an adjustment to a basal rate of a therapy delivery device based on the current risk metric associated with the detected glucose state and a reference risk metric associated with a reference glucose level.

19 Claims, 11 Drawing Sheets

(51) Int. Cl.
*A61M 5/142* (2006.01)
*A61M 5/172* (2006.01)
(52) U.S. Cl.
CPC ... *A61M 2205/502* (2013.01); *A61M 2205/52* (2013.01); *A61M 2230/201* (2013.01)

(56) References Cited

U.S. PATENT DOCUMENTS

| | | |
|---|---|---|
| 7,291,107 B2 | 11/2007 | Hellwig et al. |
| 7,395,158 B2 | 7/2008 | Monfre et al. |
| 7,785,313 B2 | 8/2010 | Mastrototaro |
| 8,579,854 B2 | 11/2013 | Budiman et al. |
| 8,579,879 B2 | 11/2013 | Palerm et al. |
| 8,684,922 B2 | 4/2014 | Tran |
| 8,734,422 B2 | 5/2014 | Hayter |
| 8,843,321 B2 | 9/2014 | Duke et al. |
| 8,977,504 B2 | 3/2015 | Hovorka |
| 9,247,901 B2 | 2/2016 | Kamath et al. |
| 2002/0106709 A1 | 8/2002 | Potts et al. |
| 2004/0167464 A1 | 8/2004 | Ireland et al. |
| 2006/0047192 A1 | 3/2006 | Hellwig et al. |
| 2009/0105572 A1 | 4/2009 | Malecha |
| 2010/0262434 A1 | 10/2010 | Shaya |
| 2011/0071464 A1 | 3/2011 | Palerm |
| 2011/0184267 A1 | 7/2011 | Duke et al. |
| 2011/0257627 A1 | 10/2011 | Hovorka |
| 2011/0313674 A1 | 12/2011 | Duke et al. |
| 2012/0165638 A1 | 6/2012 | Duke et al. |
| 2012/0166126 A1 | 6/2012 | Engelhardt et al. |
| 2014/0005505 A1 | 1/2014 | Peyser et al. |
| 2014/0066884 A1 | 3/2014 | Keenan et al. |
| 2014/0066887 A1 | 3/2014 | Mastrototaro et al. |
| 2014/0081103 A1 | 3/2014 | Schaible |
| 2014/0083867 A1 | 3/2014 | Schaible |
| 2014/0088392 A1 | 3/2014 | Bernstein et al. |
| 2014/0100435 A1 | 4/2014 | Duke et al. |
| 2014/0118138 A1 | 5/2014 | Cobelli et al. |
| 2014/0187887 A1 | 7/2014 | Dunn et al. |
| 2014/0188400 A1 | 7/2014 | Dunn et al. |
| 2014/0221966 A1 | 8/2014 | Buckingham et al. |
| 2014/0235981 A1 | 8/2014 | Hayter |
| 2015/0273147 A1 | 10/2015 | Duke et al. |

FOREIGN PATENT DOCUMENTS

| | | |
|---|---|---|
| WO | 2013/032965 A1 | 3/2013 |
| WO | 2014/106263 A2 | 7/2014 |
| WO | 2015073211 A1 | 5/2015 |
| WO | 2015183689 A1 | 12/2015 |

OTHER PUBLICATIONS

Written Opinion pertaining to PCT application No. PCT/US2017/031661, filed May 9, 2017, 11 pages.
Kovatchev, B.P., et al., Symmetrization of the Blood Glucose Measurement Scale and Its Applications, Diabetes American Diabetes Association, vol. 20., No. 11, Nov. 1, 1997, pp. 1655-1658, USA.
International Search Report pertaining to PCT application No. PCT/US2017/031662, filed May 9, 2017, 6 pages.
Written Opinion pertaining to PCT application No. PCT/US2017/031662, filed May 9, 2017, 9 pages.
Hughes, et al., Hypoglycemia Prevention via Pump Attenuation and Red-Yellow-Green "Traffic" Lights Using Continuous Glucose Monitoring and Insulin Pump Data, Journal of Diabetes Science and Technology, vol. 4, No. 5, Sep. 1, 2010, pp. 1146-1155, USA.
U.S. Non-Final Office Action dated Sep. 5, 2017 pertaining to U.S. Appl. No. 14/677,148, 13 Pages.
International Search Report dated Aug. 21, 2017, pertaining to PCT/US2017/029072, filed Apr. 24, 2017, 6 pages.
Written Opinion dated Aug. 21, 2017, pertaining to PCT/US2017/029072, filed Apr. 24, 2017, 14 pages.
Jaramillo et al., Prediction of Postprandial Blood Glucose Under Intra-Patient Variability and Uncertainty and Its Use in the Design of Insulin Disposing Strategies for Type I Diabetic Patients, Jul. 22, 2011, pp. 1-178, URL:http://dugi-doc.udg.edu/bitstream/handle.
Bruno Sinopoli, et al., Kalman Filtering With Intermittent Observations, DARPA under grant F33615-01-C-1895, 28 pages.
David Di Ruscio, Closed and Open Loop Subspace System Identification of the Kalman Filter, 2009 Norwegian Society of Automatic Control, vol. 30, No. 2 , 2009, pp. 71-86, ISSN 1890-1328, Norway.
J. Zico Kolter, et al., A Probabilistic Approach to Mixed Open-loop and Closed-loop Control, with Application to Extreme Autonomous Driving, Computer Science Department, Stanford University, California (kolter@cs.stanford.edu) 7 pages, USA.
Chiara Toffanin, et al., Artificial Pancreas: Model Predictive Control Design from Clinical Experience, Journal of Diabetes Science and Technology, pp. 1470-1483, vol. 7, Issue 6, Nov. 2013, USA.
Signe Schmidt, et al., Model-Based Closed-Loop Glucose Control in Type 1 Diabetes: The DiaCon Experience, Journal of Diabetes Science and Technology, pp. 1255-1264, vol. 7, Issue 5, Sep. 2013, USA.
Schwartz et al., "Use of Automated Bolus Calculators for Diabetes Management," Diabetes Management, Touch Medical Media 2013, 92-95.
International Search Report and Written Opinion completed Jun. 10, 2016 pertaining to PCT/US2016/025502 filed Apr. 1, 2016.
Kovatchev et al., "Symmetrization of the Blood Glucose Measurement Scale and Its Applications,", Diabetes Care, 1997, vol. 20, No. 11, 1655-1658.
Lucero et al., "On the Registration of Time and the Patterning of Speech Movements," Journal of Speech, Language, and Hearing Research 40: 1111-1117.
Ward, "Hierarchical Grouping to Optimize an Objective Function," Journal of the American Statistical Association, 1963, vol. 58, Issue 301, 236-244.
Kaufman et al., Finding Groups in Data: An Introduction to Cluster Analysis (1 ed.), New York: John Wiley, ISBN 0-471-87876-6 (Book).
Sakoe et al., "Dynamic Programming Algorithm Optimization for Spoken Word Recognition," IEEE Transactions on Acoustics, Speech and Signal Processing 26 (1): 43-49.
Takita et al., "Cluster Analysis of Self-Monitoring Blood Glucose Assessments in Clinical Islet Cell Transplantation fo Type 1 Diabetes," Diabetes Care, vol. 34, 2011, 1799-1803.
Pickup et al. (Continuous Subcutaneous Insulin Infusion at 25 Years, Diabetes Care 2002, 25, 593-598).
International Search Report and Written Opinion pertaining to Appln. No. PCT/US2017/019025, dated May 29, 2017.
International Search Report and Written Opinion pertaining to Appln. No. PCT/US2017/019013, dated May 30, 2017.
International Search Report and Written Opinion pertaining to Appln. No. PCT/US2017/019030, dated May 19, 2017.

RISK-BASED CONTROL-TO-RANGE

TECHNICAL FIELD

The present invention generally relates to processing glucose data measured from a person having diabetes and, in particular, for controlling adjustment of a temporary basal rate based on risk associated with a glucose state of a person with diabetes.

BACKGROUND

Many people suffer from Type I or Type II diabetes, in which the body does not properly regulate the blood glucose level. A continuous glucose monitor (CGM) allows the interstitial glucose level of a patient with diabetes to be measured on an ongoing basis, such as every few minutes. The timing and dosage of insulin to administer to the patient may be determined on the basis of measurements recorded by the CGM device. Glucose readings from CGM devices are displayed to the patient, and the patient can inject insulin or consume meals to help control the glucose level. Insulin pumps can deliver precise insulin dosages on a programmable schedule which may be adjusted by the patient or health care provider.

Hazard metrics may be derived from glucose data for assessing a hazard to the diabetic person based on a detected glucose level. For example, a known hazard metric includes the hazard function proposed in the following paper: Kovatchev, B. P. et al., *Symmetrization of the blood glucose measurement scale and its applications*, Diabetes Care, 1997, 20, 1655-1658. The Kovatchev hazard function is defined by the equation $h(g)=[1.509 \ (\log(g)^{1.0804}-5.381)]^2$, wherein g is the blood glucose concentration (in milligrams per deciliter or mg/dl) and h(g) is the corresponding penalty value. The Kovatchev function provides a static penalty (i.e., hazard) value in that the penalty depends only on the glucose level. The minimum (zero) hazard occurs at 112.5 mg/dl. The hazard with the glucose level approaching hypoglycemia rises significantly faster than the hazard with the glucose level approaching hyperglycemia.

The Kovatchev hazard function fails to account for the rate of change of the glucose level as well as the uncertainty associated with the measured glucose level. For example, a patient's hazard associated with 100 mg/dl and a rapidly falling blood glucose level is likely greater than the patient's hazard associated with 100 mg/dl with a constant glucose rate of change. Further, measured glucose results may be inaccurate due to sensor noise, sensor malfunction, or detachment of the sensor.

Various approaches have been made to control the glucose levels of diabetic people based on CGM glucose data. One approach for limiting the occurrence of hypoglycemic conditions includes an insulin pump shutoff algorithm that completely shuts off the basal insulin if the CGM glucose level drops below a low glucose threshold, such as 50 to 70 mg/dl, and later resumes the basal insulin after a few hours. However, this on/off approach adversely requires the adverse condition of crossing the low glucose threshold to occur before action is taken. Further, this approach does not take into account the speed with which the glucose is crossing the threshold, which may be problematic for patients (e.g., children, active individuals, etc.) with a high rate of glucose change.

Another approach is to alert the patient of predicted hypoglycemia, and the patient then consumes an amount of carbohydrates and waits a predetermined time period. If the system still predicts hypoglycemia the patient repeats the cycle until the system no longer predicts hypoglycemia. However, this approach makes the assumption that the patient is able to consume carbohydrates immediately upon being alerted of the predicted hypoglycemia. Further, the patient may overcorrect by consuming too many carbs, possibly leading to weight gain or to trending the glucose levels towards hyperglycemia.

Accordingly, some embodiments of the present disclosure provide a predictive approach for adjusting a therapy basal rate by mapping the risk of the estimated glucose state to an adjustment of the basal rate based on cumulative hazard values of return paths generated from a glucose state distribution around the estimated glucose state. Risk associated with the glucose state is based on the blood glucose level, the rate of change of the blood glucose level, and the standard deviations of the blood glucose level and rate of change. Further, some embodiments provide for adjusting the calculated risk for a glucose state in response to a meal bolus, an insulin bolus, and/or other events such as exercise, glucagon availability, and stress that may affect the risk of hypoglycemia or hyperglycemia.

SUMMARY

In one embodiment, a method of determining a basal rate adjustment of insulin based on risk associated with a glucose state of a person with diabetes is provided. The method includes receiving, by at least one computing device, a signal representative of at least one glucose measurement. The method also includes detecting, by the at least one computing device, a glucose state of the person based on the signal, the detected glucose state including a glucose level of the person and a rate of change of the glucose level. Further, the method includes determining, by the at least one computing device, a current risk metric associated with the detected glucose state based on a target glucose state, the target glucose state being stored in memory accessible by the at least one computing device, the current risk metric indicating a risk of at least one of a hypoglycemic condition and a hyperglycemic condition of the person. A return path is determined based on a transition from the current glucose state to the target glucose state, the return path comprising at least one intermediate glucose value associated with a return to the target glucose state. Further, a cumulative hazard value of the return path is determined, the cumulative hazard value including a sum of the hazard values of the at least one glucose value on the return path, each hazard value being indicative of a hazard associated with the corresponding intermediate glucose value. Additionally, the current risk metric is determined based on a weighted average of cumulative hazard values of return paths generated from a glucose state distribution around the detected glucose state. The method also includes identifying, by the at least one computing device, a reference glucose state and a reference risk metric associated with the reference glucose state; and calculating, by the at least one computing device, an adjustment to a basal rate of a therapy delivery device based on the current risk metric associated with the detected glucose state and the reference risk metric associated with the reference glucose level.

In another embodiment, blood glucose management device configured to determine a basal rate adjustment based on risk associated with a glucose state of a person with diabetes is provided. The device includes a non-transitory computer-readable medium storing executable instructions; and at least one processing device configured to execute the executable instructions such that, when executed by the at least one processing device, the executable instructions cause the at least one processing device to receive a signal representative of at least one glucose measurement. The executable instructions also cause the at least one processing device to detect a glucose state of the person based on the signal, the detected glucose state including a glucose level of the person and a rate of change of the glucose level. Additionally, the executable instructions cause the at least one processing device to determine a current risk metric associated with the detected glucose state based on a target glucose state, the target glucose state being stored in memory accessible by the at least one computing device, the current risk metric indicating a risk of at least one of a hypoglycemic condition and a hyperglycemic condition of the person. A return path is determined based on a transition from the current glucose state to the target glucose state, the return path comprising at least one intermediate glucose value associated with a return to the target glucose state. A cumulative hazard value of the return path is determined, the cumulative hazard value including a sum of the hazard values of the at least one glucose value on the return path, each hazard value being indicative of a hazard associated with the corresponding intermediate glucose value. The current risk metric is determined based on a weighted average of cumulative hazard values of return paths generated from a glucose state distribution around the detected glucose state. The executable instructions also cause the at least one processing device to identify a reference glucose state and a reference risk metric associated with the reference glucose state. Finally, the executable instructions also cause the at least one processing device to calculate an adjustment to a basal rate of a therapy delivery device based on the current risk metric associated with the detected glucose state and the reference risk metric associated with the reference glucose level.

BRIEF DESCRIPTION OF THE DRAWINGS

The embodiments set forth in the drawings are illustrative and exemplary in nature and not intended to limit the inventions defined by the claims. The following detailed description of the illustrative embodiments can be understood when read in conjunction with the following drawings, where like structure is indicated with like reference numerals and in which:

DETAILED DESCRIPTION

The embodiments described herein generally relate to methods and systems for determining a basal rate adjustment of insulin in a continuous glucose monitoring system of a person with diabetes and, in particular, for determining a basal rate adjustment of insulin based on risk associated with a glucose state of a person with diabetes. For the purposes of defining the present disclosure, the "measured glucose results" are the glucose levels of the person as measured by the glucose sensor; the "actual glucose level" or "true glucose measurement" is the actual glucose level of the person.

Figure 1:
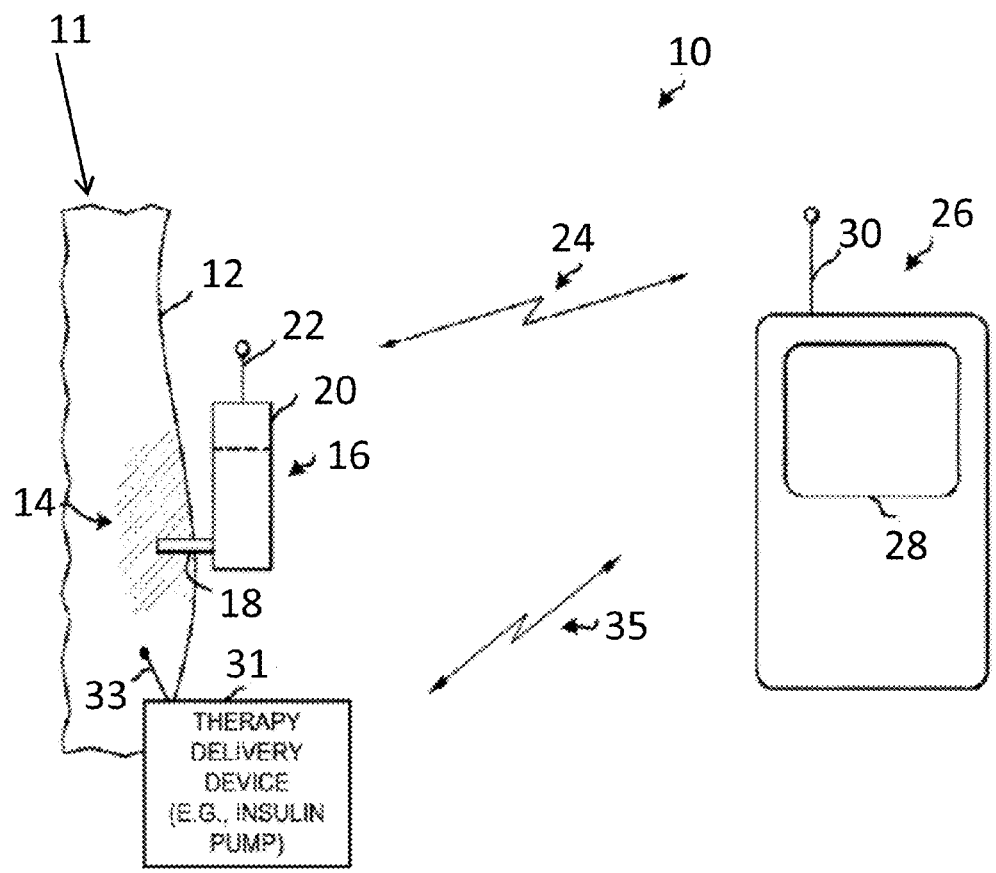
FIG. 1 illustrates a continuous glucose monitoring (CGM) system according to one or more embodiments shown and described herein.

Referring to FIG. 1, an exemplary continuous glucose monitoring (CGM) system 10 is illustrated for monitoring the glucose level of a person with diabetes (PWD) 11. In particular, CGM system 10 is operative to collect a measured glucose value at a predetermined, adjustable interval, such as every one minute, five minutes, or at other suitable intervals. CGM system 10 illustratively includes a glucose sensor 16 having a needle or probe 18 that is inserted under the skin 12 of the person. The end of the needle 18 is positioned in interstitial fluid 14, such as blood or another bodily fluid, such that measurements taken by glucose sensor 16 are based on the level of glucose in interstitial fluid 14. Glucose sensor 16 is positioned adjacent the abdomen of the person or at another suitable location. Furthermore, the glucose sensor 16 may be periodically calibrated in order to improve its accuracy. This periodic calibration may help correct for sensor drift due to sensor degradation and changes in the physiological condition of the sensor insertion site. Glucose sensor 16 may comprise other components as well, including but not limited to a wireless transmitter 20 and an antenna 22. Glucose sensor 16 may alternatively use other suitable devices for taking measurements, such as, for example, a non-invasive device (e.g., infrared light sensor). Upon taking a measurement, glucose sensor 16 transmits the measured glucose value via a communication link 24 to a computing device 26, illustratively a blood glucose (bG) management device 26. The bG management device 26 may also be configured to store in memory 39 a plurality of measured glucose results received from the glucose sensor 16 over a period of time.

CGM system 10 further includes a therapy delivery device 31, illustratively an insulin infusion pump 31, for delivering therapy (e.g., insulin) to the person. Insulin pump 31 is in communication with management device 26 via a communication link 35, and management device 26 is able to communicate bolus and basal rate information to insulin pump 31. Insulin pump 31 includes a catheter 33 having a needle that is inserted through the skin 12 of the person 11 for injecting the insulin. Insulin pump 31 is illustratively positioned adjacent the abdomen of the person or at another suitable location. Similar to glucose sensor 16, infusion pump 31 also includes a wireless transmitter and an antenna for communication with management device 26. Insulin pump 31 is operative to deliver basal insulin (e.g., small doses of insulin continuously or repeatedly released at a basal rate) and bolus insulin (e.g., a surge dose of insulin, such as around a meal event, for example). The bolus insulin may be delivered in response to a user input triggered by the user, or in response to a command from management device 26. Similarly, the basal rate of the basal insulin is set based on user input or in response to a command from management device 26. Infusion pump 31 may include a display for displaying pump data and a user interface providing user controls. In an alternative embodiment, insulin pump 31 and glucose sensor 16 may be provided as a single device worn by the patient, and at least a portion of the logic provided by processor or microcontroller may reside on this single device. Bolus insulin may also be injected by other means, such as manually by the user via a needle.

In one embodiment, such a CGM system 10 is referred to as an artificial pancreas system that provides closed loop or semi-closed loop therapy to the patient to approach or mimic the natural functions of a healthy pancreas. In such a system, insulin doses are calculated based on the CGM readings from the glucose sensor 16 and are automatically delivered to the patient based on the CGM reading. For example, if the CGM indicates that the user has a high blood glucose level or hyperglycemia, the system can calculate an insulin dose necessary to reduce the user's blood glucose level below a threshold level or to a target level and automatically deliver the dose. Alternatively, the system can automatically suggest a change in therapy such as an increased insulin basal rate or delivery of a bolus, but can require the user to accept the suggested change prior to delivery. If the CGM data indicates that the user has a low blood glucose level or hypoglycemia, the system can, for example, automatically reduce a basal rate, suggest to the user to reduce a basal rate, automatically deliver or suggest that the user initiate the delivery of an amount of a substance such as, e.g., a hormone (glucagon) to raise the concentration of glucose in the blood, suggest that the user, e.g., ingest carbohydrates and/or automatically take other actions and/or make other suggestions as may be appropriate to address the hypoglycemic condition, singly or in any desired combination or sequence. In some embodiments, multiple medicaments can be employed in such a system such as a first medicament, e.g., insulin, that lowers blood glucose levels and a second medicament, e.g., glucagon, which raises blood glucose levels.

Communication links 24, 35 are illustratively wireless, such as a radio frequency ("RF") or other suitable wireless frequency, in which data and controls are transmitted via electromagnetic waves between sensor 16, therapy delivery device 31, and management device 26. Bluetooth® is one exemplary type of wireless RF communication system that uses a frequency of approximately 2.4 Gigahertz (GHz). Another exemplary type of wireless communication scheme uses infrared light, such as the systems supported by the Infrared Data Association® (IrDA®). Other suitable types of wireless communication may be provided. Furthermore, each communication link 24, 35 may facilitate communication between multiple devices, such as between glucose sensor 16, computing device 26, insulin pump 31, and other suitable devices or systems. Wired links may alternatively be provided between devices of system 10, such as, for example, a wired Ethernet link. Other suitable public or proprietary wired or wireless links may be used.

Figure 2:
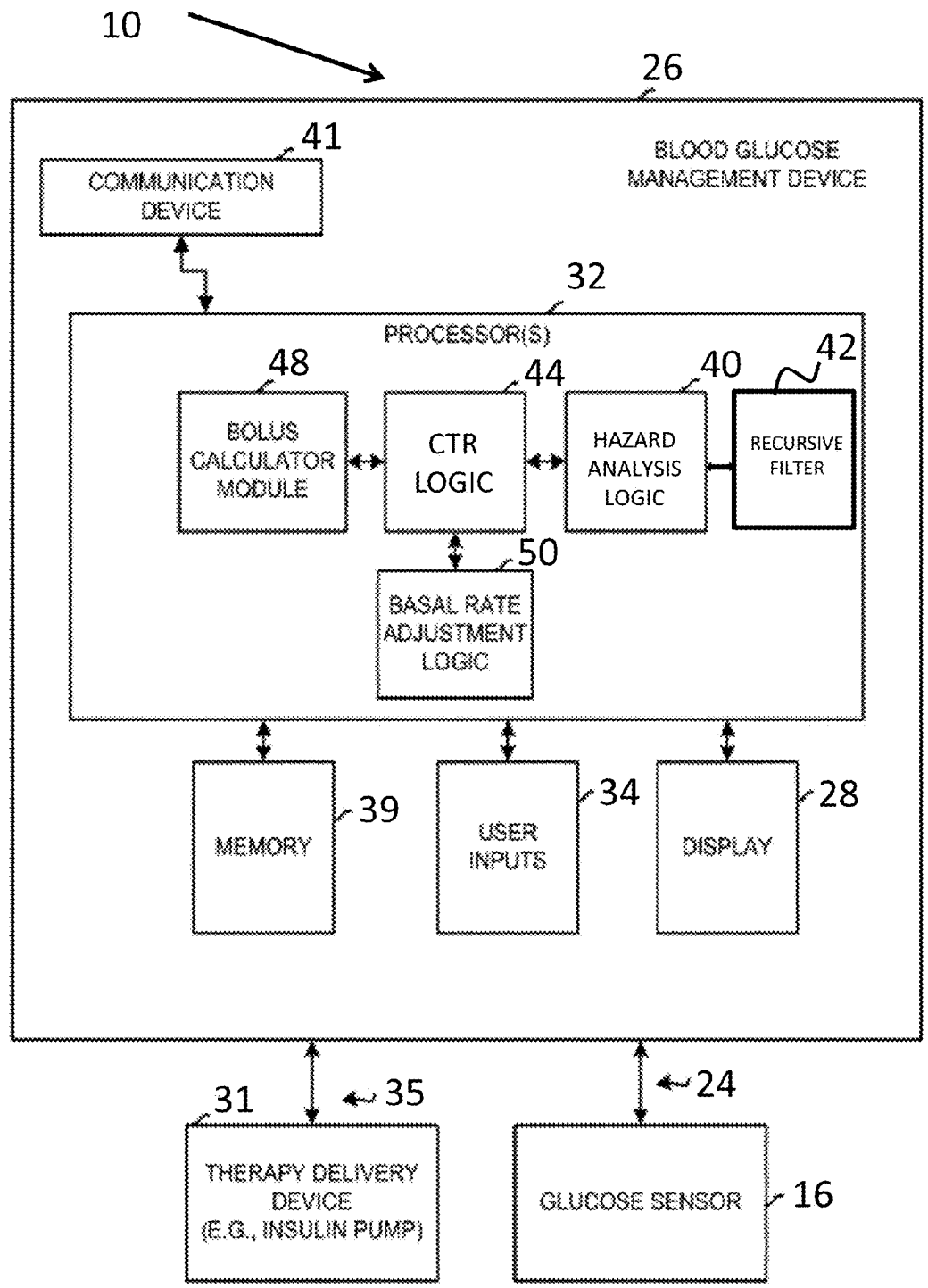
FIG. 2 illustrates an exemplary blood glucose management device, therapy delivery device, and glucose sensor of the CGM system of FIG. 2, the blood glucose management device including a bolus calculator module, control-to-range logic, hazard analysis logic, a recursive filter, and basal rate adjustment logic.

FIG. 2 illustrates an exemplary management device 26 of the CGM system 10 of FIG. 2. Management device 26 includes at least one microprocessor or microcontroller 32 that executes software and/or firmware code stored in memory 39 of management device 26. The software/firmware code contains instructions that, when executed by the microcontroller 32 of management device 26, causes management device 26 to perform the functions described herein. Management device 26 may alternatively include one or more application-specific integrated circuits (ASICs), field-programmable gate arrays (FPGAs), digital signal processors (DSPs), hardwired logic, or combinations thereof. While management device 26 is illustratively a glucose monitor 26, other suitable management devices 26 may be provided, such as, for example, desktop computers, laptop computers, computer servers, personal data assistants ("PDA"), smart phones, cellular devices, tablet computers, infusion pumps, an integrated device including a glucose measurement engine and a PDA or cell phone, etc. Although management device 26 is illustrated as a single management device 26, multiple computing devices may be used together to perform the functions of management device 26 described herein.

Memory 39 is any suitable computer readable medium that is accessible by microcontroller 32. Memory 39 may be a single storage device or multiple storage devices, may be located internally or externally to management device 26, and may include both volatile and non-volatile media. Further, memory 39 may include one or both of removable and non-removable media. Exemplary memory 39 includes random-access memory (RAM), read-only memory (ROM), electrically erasable programmable ROM (EEPROM), flash memory, CD-ROM, Digital Versatile Disk (DVD) or other optical disk storage, a magnetic storage device, or any other suitable medium which is configured to store data and which is accessible by management device 26.

The microcontroller 32 may also include additional programming to allow the microcontroller 32 to learn user preferences and/or user characteristics and/or user history data. This information can be utilized to implement changes in use, suggestions based on detected trends, such as, weight gain or loss. The microcontroller 32 can also include programming that allows the device 26 to generate reports, such as reports based upon user history, compliance, trending, and/or other such data. Additionally insulin infusion pump 31 embodiments of the disclosure may include a "power off" or "suspend" function for suspending one or more functions of the device 26, such as, suspending a delivery protocol, and/or for powering off the device 26 or the delivery mechanism thereof. For some embodiments, two or more microcontrollers 32 may be used for controller functions of insulin infusion pump 31, including a high power controller and a low power controller used to maintain programming and pumping functions in low power mode, in order to save battery life.

Management device 26 further includes a communication device 41 operatively coupled to microcontroller 32. Communication device 41 includes any suitable wireless and/or wired communication module operative to transmit and receive data and controls over communication links 24, 35 between device 26 and glucose sensor 16 and insulin pump 31. In one embodiment, communication device 41 includes an antenna 30 (FIG. 1) for receiving and/or transmitting data wirelessly over communication links 24, 35. Management device 26 stores in memory 39 measured glucose results and other data received from glucose sensor 16 and/or insulin pump 31 via communication device 41.

Management device 26 includes one or more user input device(s) 34 for receiving user input. Input device(s) 34 may include pushbuttons, switches, a mouse pointer, keyboard, touchscreen, or any other suitable input device. Display 28 is operatively coupled to microcontroller 32, and may comprise any suitable display or monitor technology (e.g., liquid crystal display, etc.) configured to display information provided by microcontroller 32 to a user. Microcontroller 32 is configured to transmit to display 28 information related to the detected glucose state of the person, the risk associated with the glucose state, and basal rate and bolus information. The glucose state may include the estimated glucose level and the estimated rate-of-change of the glucose level, as well as an estimate of the quality or uncertainty of the estimated glucose level. Moreover, the displayed information may include warnings, alerts, etc. regarding whether the estimated or predicted glucose level of the person is hypoglycemic or hyperglycemic. For example, a warning may be issued if the person's glucose level falls below (or is predicted to fall below) a predetermined hypoglycemic threshold, such as 50 to 70 milligrams of glucose per deciliter of blood (mg/dl). Management device 26 may also be configured to tactilely communicate information or warnings to the person, such as for example by vibrating.

In one embodiment, management device 26 is in communication with a remote computing device (not shown), such as at a caregiver's facility or a location accessible by a caregiver, and data (e.g., glucose data or other physiological information) is transferred between them. In this embodiment, management device 26 and the remote device are configured to transfer physiological information through a data connection such as, for example, via the Internet, cellular communications, or the physical transfer of a memory device such as a diskette, USB key, compact disc, or other portable memory device.

Microcontroller 32 also includes control-to-range logic 44. A control-to-range system reduces the likelihood of a hypoglycemic event or a hyperglycemic event by adjusting insulin dosing only if the PWD's 11 glucose level approaches the low or high glucose thresholds.

Microcontroller 32 includes hazard analysis logic 40 that calculates target return paths from a plurality of initial glucose states to a target glucose state based on cumulative hazard values. The target glucose state is illustratively an optimal or ideal glucose state having no associated hazard or risk, such as a glucose level of 112.5 mg/dl and a glucose rate-of-change of zero, although any suitable target glucose state may be identified. Each target return path is comprised of a plurality of intermediate glucose states that are to be encountered during a transition from the initial glucose state to the target glucose state. Cumulative penalty values associated with the target return paths are stored in memory 76 that may be used as a lookup table. Calculation of cumulative penalty values is discussed infra.

In some embodiments, inaccurate glucose measurements may result from malfunction and/or noise associated with glucose sensor 24. As such, hazard analysis logic 40 also analyzes the probability of accuracy of the detected glucose state provided with glucose sensor 24. Hazard analysis logic 40 may use any suitable probability analysis tool to determine the probability of accuracy of a measured glucose result, such as a hidden Markov model. Based on the determined probability of accuracy, hazard analysis logic 40 estimates the glucose level and the glucose rate of change of the person using a recursive filter 42. In particular, recursive filter 42, such as a Kalman filter, for example, weights the detected glucose state, including the glucose level and rate of change, with the determined probability of glucose sensor accuracy. Based on the probability of glucose sensor accuracy, recursive filter 42 calculates an uncertainty measure of the estimated glucose state. The uncertainty measure is indicative of the quality of the estimated glucose state. For a series of detected glucose states, the uncertainty for each state may vary.

Microcontroller 32 of FIG. 2 further includes a bolus calculator module 48 that calculates bolus recommendations and a maximum allowed glucose level of a user which may be displayed to a user via display 28. Management device 26 maintains a record in memory 39 of historical data for the user accumulated over time leading up to the current time. The historical data includes blood glucose history, prescription data, prior bolus recommendations, prior administered boluses, prior basal rates, glucose sensitivity factors for the user's sensitivity to insulin and carbohydrates, blood glucose responses to prior boluses and meal events, other user health and medical data, and the time stamp of each event and data recordation. The history data includes patient recorded information such as meal events, amount of carbohydrates consumed, confirmations of bolus deliveries, medications, exercise events, periods of stress, physiological events, manual insulin injections, and other health events, entered via user inputs 34. Bolus calculator module 48 uses the historical data to more accurately and efficiently determine the recommended insulin bolus and/or carbohydrate amount.

The bolus calculator module 48 determines a recommended bolus, such as an insulin correction bolus or a meal bolus, particular to the user based on the current glucose state, the history data, and user input. A suggested meal bolus (e.g., carbohydrate amount) may be in response to a detected or predicted hypoglycemic condition. A suggested correction bolus of insulin may be in response to the detected glucose exceeding the maximum allowable glucose level. The actual amount of carbohydrates consumed and the actual amount of insulin administered may be confirmed by the user as information entered via user inputs 34 and recorded in memory 39 with other history data. The recommended bolus may be displayed on display 28.

Figure 3:
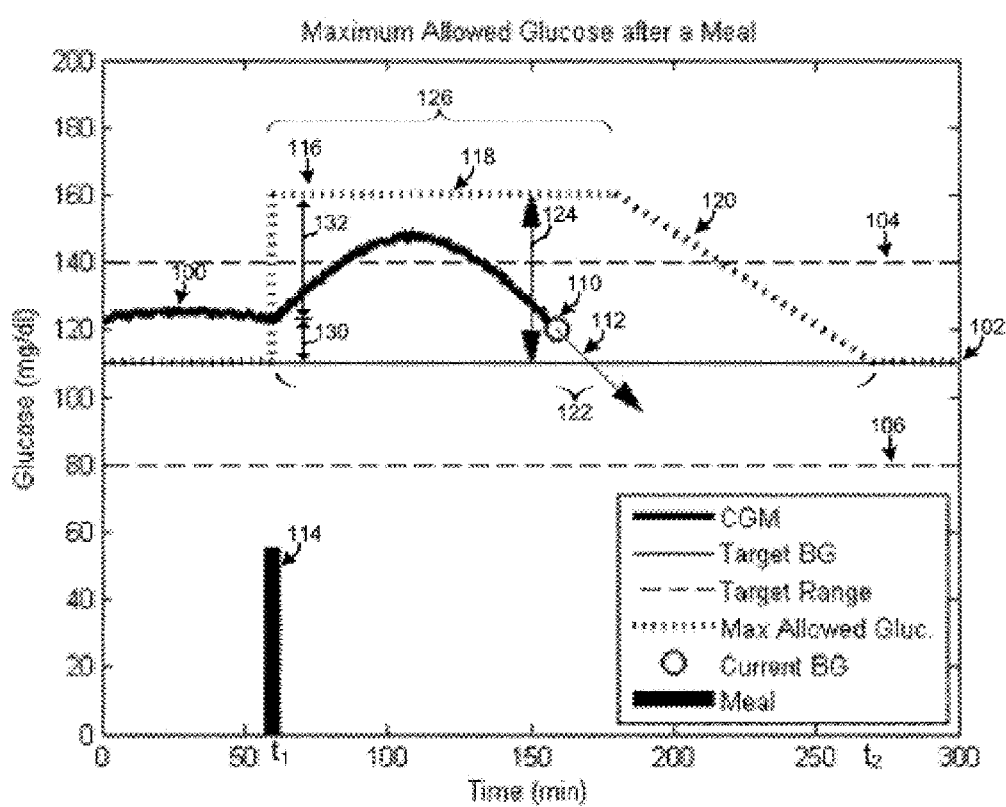
FIG. 3 illustrates a graph plotting an exemplary CGM trace and an adjusted maximum allowed glucose following a meal event.

Referring to FIG. 3, an exemplary CGM trace 100 is illustrated, wherein the x-axis represents time in minutes and the y-axis represents glucose in mg/dl. CGM trace 100 comprises a series of detected glucose levels measured over a period. In the illustrated embodiment, CGM trace 100 represents filtered glucose levels, i.e., glucose levels that are estimated based on the measured glucose levels weighted with the probably of sensor accuracy. A most recent estimated glucose level 110 has an associated negative rate of change indicated with arrow 112. Bolus calculator module 48 determines the target glucose level 102 and a target range of glucose levels indicated with an upper glucose limit 104 and a lower glucose limit 106. For illustrative purposes, target glucose level 102 is 110 mg/dl, upper glucose limit 104 is 140 mg/dl, and lower glucose limit 106 is 80 mg/dl, although other suitable values may be provided. Bolus calculator module 48 may determine target glucose level 102 and limits 104, 106 based at least in part on the user's history data described herein. Management device 26 uses the trending glucose data of CGM trace 100 to recommend corrective action to move the blood glucose towards the target glucose level 102. The target glucose level 102 of FIG. 3 corresponds to the maximum allowed glucose before time $t_1$ and after time $t_2$, i.e., when there has not been any recent meals or correction boluses. Between times $t_1$ and $t_2$, the maximum allowed glucose is adjusted based on a meal event 114 or other suitable events.

At time $t_1$, meal event 114 occurs when the user consumes a meal and enters carbohydrate data into management device 26 indicating the amount of carbohydrates consumed with the meal. In some instances, an insulin bolus is administered at about the time of the meal event 114 to offset the expected increase in glucose levels resulting from the meal. Bolus calculator module 48 determines a projected glucose level rise and a duration of the glucose rise based on the carbohydrates consumed, the insulin correction bolus (if administered), and the user's historical data related to glucose swings following meals and insulin injections. Based on the projected glucose rise, bolus calculator module 48 determines an allowed rise value 124, an offset time value 126, and an acting time value 122. The allowed rise value 124 may be based on other events, such as a glucagon injection, exercise, sleep, driving, or time of day, for example.

The allowed rise value 124 is the amount by which the glucose level of the user may be allowed to increase with respect to the target glucose level 102 as a result of the carbohydrate intake and insulin bolus. In some embodiments, the allowed rise value 124 is the combination of a correction delta glucose value 130 resulting from an insulin bolus and a meal rise value 132 resulting from the meal event 114. The correction delta glucose value 130 is the difference between the current glucose level and the target glucose level 102 at the time of the insulin bolus to allow time for the glucose level to decrease following insulin. As illustrated, the allowed rise value 124 is constant (see line 118) for a first predetermined amount of time after the meal and insulin administration, i.e., offset time 126, and then decreases linearly (see slope 120) following the offset time 126. The total time that the meal and insulin dose have an effect on the bG levels of a patient is the acting time 122. FIG. 3 illustrates a trapezoid-shaped graph 116 of the allowed rise value 124 accounting for the effect of a dose of insulin and meal event.

The maximum allowed glucose increases based on allowed rise value 124 and follows plot 116 of FIG. 3. As such, bolus calculator module 48 expands the range of allowable glucose levels after a meal event for the duration of the acting time 122 according to plot 116. The allowed rise value 124 illustratively has an initial height of 50 mg/dl, but could have other suitable heights based on the meal size, the insulin, and the user's typical reactions to boluses from the historical data. In some embodiments, for meal events above a threshold amount of carbohydrates, the meal rise value 132 is fixed. As one example, the offset time 126 is about two hours, and the acting time 122 is about three to five hours, depending on the user, the meal size, and the insulin bolus.

Referring again to FIG. 2, management device 26 further includes basal rate adjustment logic 50 operative to calculate and adjust a basal rate based on the current glucose state and the risk associated with the current glucose state. Management device 26 transmits an adjustment to the basal rate in a control signal to insulin pump 31 via communication link 35, and insulin pump 31 adjusts the current insulin basal rate based on the adjustment. Alternatively, the adjusted basal rate may be displayed to the user, and the user manually adjusts the basal rate of insulin pump 31. In one or more embodiment, the adjustment is a percent reduction to the initial, unadjusted or nominal basal rate based on a risk of hypoglycemia or a percent increase to the initial, unadjusted or nominal basal rate based on risk of hyperglycemic conditions.

The basal rate adjustment logic 50 determines whether the basal rate is to be adjusted. If an adjusted basal rate is proper, basal rate adjustment logic 50 calculates an adjusted basal rate and management device 26 transmits a control signal to insulin pump 31 to cause insulin pump 31 to deliver insulin at the adjusted basal rate. Alternatively, management device 26 may display the adjusted basal rate to the user to prompt the user for manual adjustment of the insulin pump 31. In some embodiments, the implementation of the adjusted basal rate may be overridden by the user via manual control of the insulin pump 31.

Figure 4:
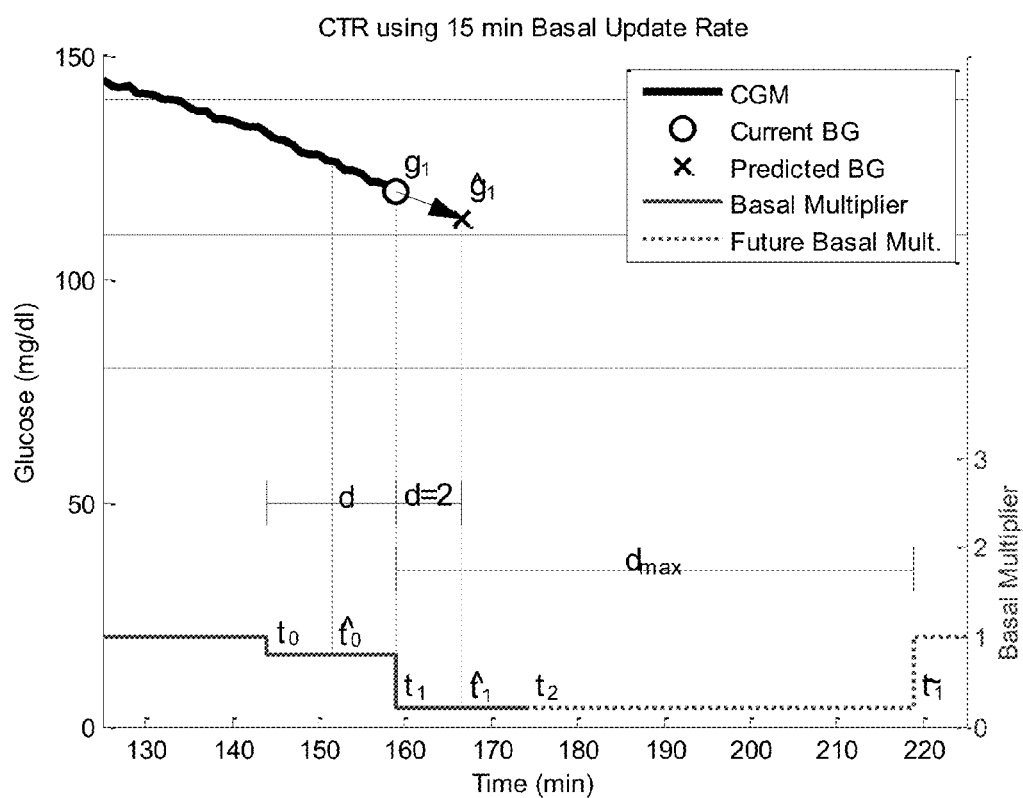
FIG. 4 illustrates a graph plotting periodic updates to the basal rate.

A basal rate multiplier adjustment is determined from a glucose measurement. In one or more embodiments, the basal rate multiplier is changed at a fixed interval, for example 15 minutes. The glucose value and glucose rate-of-change are used to predict the glucose value at the midpoint of the next fixed interval when calculating a new basal rate multiplier. FIG. 4 shows an example with a fixed interval of length d so at time $t_1$ the glucose value and trend at $g_1$ is used to predict the value at time $\hat{t}_1$. This value, $\hat{g}_1$, is then used to calculate the basal rate multiplier that will be used between time $t_1$ and $t_2$.

Determination of the basal rate multiplier for implementation begins with estimating the current glucose state. The full glucose state includes the glucose level, glucose rate-of-change, and a covariance matrix indicating the spread of the glucose level and glucose rate-of-change. These values are provided by the recursive filter 42. If the noise of a sensor is close to constant, then the glucose state can be reduced to just the glucose and rate-of-change.

In determining adjustments to the basal rate, it is assumed that the CGM controller receives a measurement every minute (or other periodic period), but communicates with the insulin pump less frequently. Once a temporary basal rate (TBR) for a period has been transmitted to the pump, the algorithm waits at least d minutes before another TBR command is sent. In at least one embodiment d is equal to 15 minutes such that the TBR is updated on a periodic 15 minute basis. In further embodiments, d is equal to 10 minutes, 5 minutes, 2 minutes, or 1 minute, for example. It will be appreciated that d may be adjusted based on the individual needs of the PwD.

Figure 5:
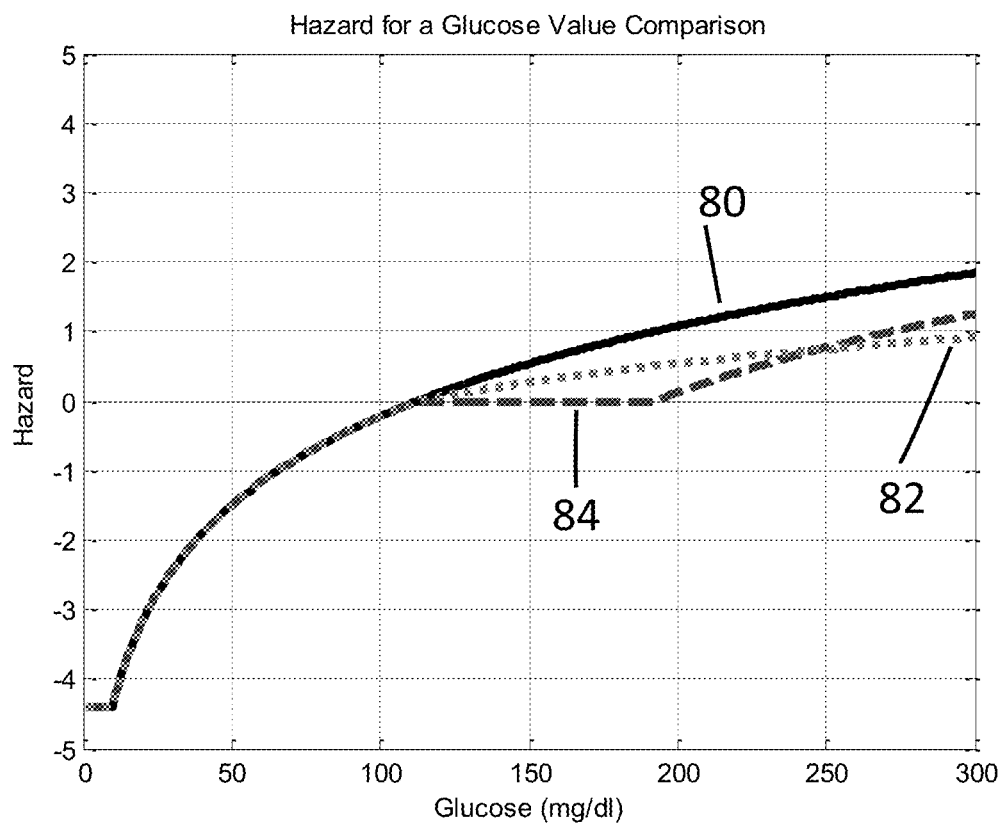
FIG. 5 illustrates a graph plotting a hazard function with exemplary hyperglycemic aggressiveness and hyperglycemic shift adjustments.
Figure 6:
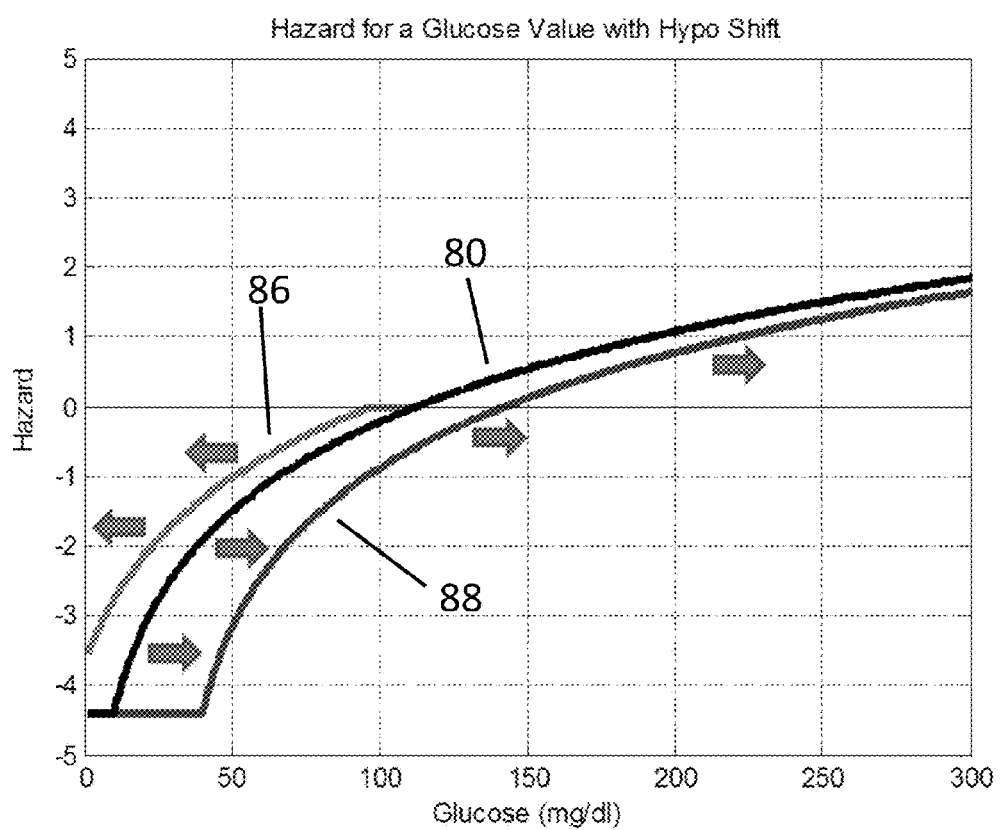
FIG. 6 illustrates a graph plotting a hazard function with hypoglycemic shifts due to exercise or availability of glucagon.

As previously discussed, microcontroller 32 includes hazard analysis logic 40 that calculates target return paths from a plurality of initial glucose states to a target glucose state based on cumulative hazard values. FIGS. 5 and 6 illustrate an exemplary hazard function 80 for calculating a hazard value for a given glucose level ultimately utilized in determination of the cumulative hazard value. The hazard function 80 is defined by the following equation:

$$h(g)_{hyper} = \max(\alpha_{hyper} \cdot \alpha(\log(\max(g - \Delta g_{hyper} - \max(\Delta g_{hypo}, 0), 1))^c - \beta), 0) \quad (1)$$

$$h(g)_{hypo} = \min(\alpha(\log(\max(g - \Delta g_{hypo}, 1))^c - \beta), 0) \quad (2)$$

$$h(g) = \begin{cases} h_{MAX} & \text{if } g - \Delta g_{hyper} - \max(\Delta g_{hypo}, 0) \geq g_{MAX} \\ h_{MIN} & \text{if } g - \Delta g_{hypo} \leq g_{MIN} \\ h(g)_{hyper} & \text{if } h(g)_{hypo} \geq 0 \\ h(g)_{hypo} & \text{if } h(g)_{hypo} < 0 \end{cases} \quad (3)$$

where g is the blood glucose value (mg/dl) shown on the x-axis, h(g) is the corresponding hazard value shown on the y-axis, $\Delta g_{hyper}$ is a hyperglycemic shift, $\Delta g_{hyper}$ is a hypoglycemic shift, $h_{MAX}$ is a maximum hazard, $h_{MIN}$ is a minimum hazard, $\alpha_{hyper}$ is the hyperglycemic control aggressiveness, and $\alpha$, $\beta$, and c are process variables. In the illustrated embodiment, the variables $\alpha$, $\beta$, and c are defined as follows: $\alpha=1.509$, $\beta=5.381$, and $c=1.084$. $g_{MAX}$ is a glucose value above which no additional incremental hazard is calculated above $h_{MAX}$ and similarly $g_{MIN}$ is a glucose value below which no additional incremental hazard is calculated above $h_{MIN}$. Test cases of hazard functions for a hyperglycemic range $(h(g)_{hyper})$ and a hypoglycemic range $(h(g)_{hypo})$ are generated. The h(g) function determines if $h_{MAX}$, $h_{MIN}$, $h(g)_{hyper}$, or $h(g)_{hypo}$ should be implemented as the final hazard value for the tested blood glucose value.

Implementation of $g_{MAX}$ and $g_{MIN}$ in the determination of $h_{MAX}$ and $h_{MIN}$ respectively prevent excessively positive or negative hazard values for extreme blood glucose values. In one or more embodiments $g_{MAX}$ is set at 600 mg/dl and $h_{MAX}$ is the $h(g)_{hyper}$ associated with $g_{MAX}$. Similarly, in one or more embodiments $g_{MIN}$ is set at 10 mg/dl and $h_{MIN}$ is the $h(g)_{hypo}$ associated with $g_{MIN}$. As such, if g exceeds $g_{MAX}$ or drops below $g_{MIN}$, the hazard value associated with the blood glucose value is prevented from exceeding the range defined by $h_{MAX}$ and $h_{MIN}$.

Patients with diabetes exhibit varying degrees of insulin sensitivity. As such the parameter $\alpha_{hyper}$ provides functionality to adjust the aggressiveness of the hyperglycemic hazard function $(h(g)_{hyper})$ to account for the varying insulin sensitivities. With reference to FIG. 5, a nominal hazard function 80 is shown along with a hazard function with reduced $\alpha_{hyper}$ 82.

With reference to FIG. 5, $\Delta g_{hyper}$ shifts the hazard function 80 in the hyperglycemic region (positive hazard values) to account for a recent meal or correction bolus. Hyper shift hazard function 84 illustrates a shift in the hazard function after a previous meal or correction bolus.

With reference to FIG. 6, $\Delta g_{hypo}$ shifts the hazard function to account for recent exercise, availability of glucagon, or an excessive correction bolus, for example. For safety, the hyperglycemic hazard region that is associated with an increase in insulin is never shifted to the left. When glucagon is present the hypoglycemic hazard region is shifted to the left 86 because the glucagon accounts for a portion of the hypoglycemic hazard. The hyperglycemic hazard is not shifted in such instance because insulin administration should not be increased due to glucagon. In the case of exercise, for example, the hypoglycemic hazard is increased and the curve is shifted to the right 88. In this case the entire hazard curve is shifted.

The cumulative hazard value of a return path from the current glucose state to the target glucose state is calculated by summing the hazard values of the glucose values on the path between the current glucose state and the target glucose state. The path is constrained by limiting the maximum allowed glucose acceleration. Additionally, the target is assumed to have a rate-of-change of zero as once the target glucose state is reached it is desired to remain at the target glucose state and not oscillate above and below the target glucose state.

The return path of minimum risk between the glucose state and the target is the fastest path. This return path uses the maximum allowed glucose accelerations, both positive and negative glucose accelerations, to return to the target glucose state. The closed form solution to the return path generation is composed of a time period with one extreme of the allowed glucose accelerations followed by the opposite extreme.

If a positive hypoglycemic shift is being used then the hypoglycemic shift must be added to the target glucose to get the shifted glucose target. This is necessary to correctly shift the hypoglycemic risk as the glucose target represents the blood glucose level where the hazard shifts from positive (hyperglycemic) to negative (hypoglycemic). The adjustment of the target glucose to the shifted glucose target is defined by the following equation:

$$\hat{g}_t = g_t + \max(\Delta g_{hypo}, 0) \tag{4}$$

where $\hat{g}_t$ is the shifted glucose target, $g_t$ is the nominal glucose target, and $\Delta g_{hypo}$ is the hypoglycemic shift. The maximum function in equation 4 prevents a negative hypoglycemic shift from being added to the target glucose and instead uses a hypoglycemic shift of zero resulting in $\hat{g}_t$ and $g_t$ being equal.

As an initial matter, the generalized form of the return path must be determined. The return path may have an initial positive glucose acceleration followed by a negative glucose acceleration or may have an initial negative glucose acceleration followed by a positive glucose acceleration. The generalized form of the return path may be determined by solving which of equation 5 and equation 6, presented infra, returns a real number solution.

$$T^{\pm} = t_1^{\pm} + t_2^{\pm} \tag{5}$$

$$T^{\mp} = t_1^{\mp} + t_2^{\mp} \text{ where} \tag{6}$$

$$t_1^{\pm} = \frac{\sqrt{\ddot{g}_n(\ddot{g}_p - \ddot{g}_n)(-\dot{g}^2 + 2\ddot{g}_p - 2\hat{g}_t\ddot{g}_p)} - \dot{g}\ddot{g}_p + \dot{g}\ddot{g}_n}{\ddot{g}_p(\ddot{g}_p - \ddot{g}_n)}, \tag{7}$$

$$t_2^{\pm} = \frac{\dot{g} + \ddot{g}_p t_1^{\pm}}{-\ddot{g}_n}, \tag{8}$$

$$t_1^{\mp} = \frac{\sqrt{\ddot{g}_p(\ddot{g}_n - \ddot{g}_p)(-\dot{g}^2 + 2\ddot{g}_n - 2\hat{g}_t\ddot{g}_n)} - \dot{g}\ddot{g}_n + \dot{g}\ddot{g}_p}{\ddot{g}_n(\ddot{g}_n - \ddot{g}_p)}, \tag{9}$$

$$t_2^{\mp} = \frac{\dot{g} + \ddot{g}_n t_1^{\mp}}{-\ddot{g}_p}, \tag{10}$$

$\dot{g}$ is the rate of change of the glucose level, $\ddot{g}_p$ is the maximum positive glucose acceleration, $\ddot{g}_n$ is the maximum negative glucose acceleration, and $\hat{g}_t$ is the shifted glucose target from equation 4. If equation 5 returns a real number for $T^{\pm}$ and both $t_1^{\pm}$ and $t_2^{\pm}$ are greater than or equal to zero, the return path utilizes a positive acceleration first and a negative acceleration second. Conversely, if equation 6 returns a real number for $T^{\mp}$ and both $t_1^{\mp}$ and $t_2^{\mp}$ are greater than or equal to zero, the return path utilizes a negative acceleration first and a positive acceleration second.

Once the generalized form of the return path is determined, the cumulative hazard value of the return path may be calculated. When the return path utilizes a positive acceleration first, the cumulative hazard value is defined by the following equation:

$$h(g, \dot{g}) = \sum_{t=0}^{t_1^{\pm}} h\left(g + \dot{g}t + \frac{1}{2}\ddot{g}_p t^2\right) + \sum_{t=0}^{t_2^{\pm}} h\left(\hat{g}_t + \frac{1}{2}\ddot{g}_n t^2\right) \tag{11}$$

and when the return path utilizes a negative acceleration first, the cumulative hazard value is defined by the following equation:

$$h(g, \dot{g}) = \sum_{t=0}^{t_1^{\mp}} h\left(g + \dot{g}t + \frac{1}{2}\ddot{g}_n t^2\right) + \sum_{t=0}^{t_2^{\mp}} h\left(\dot{g}_t + \frac{1}{2}\ddot{g}_p t^2\right). \quad (12)$$

Figure 7:
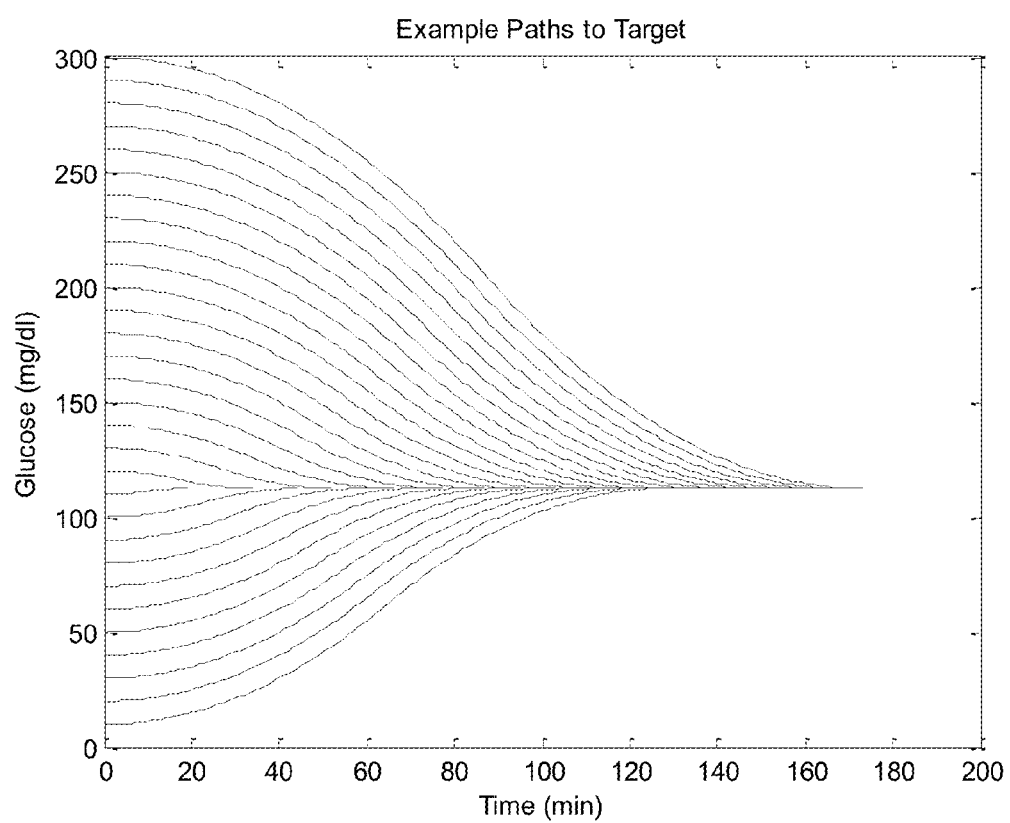
FIG. 7 illustrates a graph plotting exemplary return paths to the target glucose level.

It should be appreciated that return paths that encounter more extreme glucose values will tend to have a higher cumulative hazard value as the hazard value for each time point is higher as illustrated in FIGS. 5 and 6. For example, a blood glucose value of 225 mg/dl would have a higher hazard value than a blood glucose value of 120 mg/dl at the same glucose rate-of-change. Also, paths that take a longer time to return to the target glucose state will tend to have a higher hazard value. A path may require longer returning to the target glucose state as a result of initial glucose rate-of-change or extreme glucose values. With reference to FIG. 7, exemplary return paths for a broad range of initial glucose values where the initial rate-of-change is zero are provided. The time to the target glucose state in FIG. 7 ranges from about 20 minutes to almost 180 minutes. This amplifies the differences in cumulative hazard values for the initial glucose states. Calculating the cumulative hazard value allows for the comparison of glucose states with different glucose values and rates-of-change. Often a glucose value closer to the target glucose value has a higher hazard value than a more distant glucose value if the glucose rate-of-change is more extreme.

The cumulative hazard value provides the hazard for a specific return path from the current glucose state to the target glucose state. However, there are uncertainties in CGM blood glucose measurements from glucose sensor 16. As such, the true blood glucose measurement may vary from the blood glucose determined by the glucose sensor 16 and the specific calculated cumulative hazard value may be inaccurate with regards to the actual return path. To account for the variability in the true return path, a current risk metric is determined which accounts for variance in the CGM blood glucose measurements.

To calculate the current risk metric, a predicted glucose state at an intermediate point of the CTR period is initially determined. In various embodiments, the intermediate point of the CTR period is the true midpoint (½ of the CTR period), ¼ of the CTR period, ⅓ of the CTR period, ⅔ the CTR period, or ¾ of the CTR period. In an embodiment, the CTR is typically updated every 15 minutes resulting in the midpoint being 7.5 minutes into the 15 minute sampling interval. For short time horizons a linear prediction performs as well or better than more complicated models, so a linear prediction is used for simplicity. The rate-of-change in the glucose level is assumed to remain constant over the 7.5 min window in determining the predicted blood glucose level at the midpoint of the 15 minute sampling interval. As such, the predicted glucose level is defined by the following equation:

$$\hat{g} = g + \dot{g}\tau \quad (13)$$

where g is the initial measured blood glucose level, $\dot{g}$ is the initial rate-of-change of the glucose level, and $\tau$ is the prediction time measured from the beginning of the CTR period. The predicted glucose state is thus $[\hat{g}, \dot{g}]$.

Subsequently, a glucose state distribution around the predicted glucose state is determined. Similarly, a glucose state distribution around the current glucose state may also be determined. The samples for the glucose state distribution are selected based on the standard deviation of the distribution in the g and $\dot{g}$ directions. Generation of the glucose state distribution samples is defined by the following equations:

$$G_s = \left[g - 2\sigma_g, g - 2\sigma_g + \frac{4\sigma_g}{k}, g - 2\sigma_g + 2\frac{4\sigma_g}{k}, \right. \quad (14)$$
$$\left. g - 2\sigma_g + 3\frac{4\sigma_g}{k}, \ldots, g - 2\sigma_g + k\frac{4\sigma_g}{k}\right]$$

$$\dot{G}_s = \left[\dot{g} - 2\sigma_{\dot{g}}, \dot{g} - 2\sigma_{\dot{g}} + \frac{4\sigma_{\dot{g}}}{n}, \dot{g} - 2\sigma_{\dot{g}} + 2\frac{4\sigma_{\dot{g}}}{n}, \right. \quad (15)$$
$$\left. \dot{g} - 2\sigma_{\dot{g}} + 3\frac{4\sigma_{\dot{g}}}{n}, \ldots, \dot{g} - 2\sigma_{\dot{g}} + n\frac{4\sigma_{\dot{g}}}{n}\right]$$

where $G_s$ is the distribution of glucose values, $\dot{G}_s$ is the distribution of glucose rates of change, g is the glucose value for the current risk metric, $\dot{g}$ is the rate of change of the glucose level for the current risk metric, $\sigma_g$ is the standard deviation of g, $\sigma_{\dot{g}}$ is the standard deviation of $\dot{g}$, k is the number of divisions of $G_s$, and n is the number of divisions of $\dot{G}_s$. It will be appreciated that g may represented the current glucose level or the predicted glucose level if the glucose state distribution is desired for the current glucose state or the predicted glucose state respectively. Equation 14 and equation 15 provide a distribution of samples ranging within two standard deviations of g and $\dot{g}$. In at least one embodiment, the sampled values for g are selected by dividing the range bounded by two standard deviations by 10 and the sampled values for $\dot{g}$ are selected by dividing the range bounded by two standard deviations by 8 such that k=10 and n=8 respectivly. Other sampling ranges and frequencies may also be used such as 3 standard deviations.

The current risk metric is determined based on a weighted average of the cumulative hazard values of the return paths generated from each of the sampled glucose states. Specifically, the risk is calculated by determining the weighted average of the cumulative hazard values at each combination of points in $G_s$ and $\dot{G}_s$ and weighting them by a multivariate exponential function $w(g_s, \dot{g}_s)$. The current risk metric is defined by the following equation:

$$r = \frac{\Sigma_{G_s} \Sigma_{\dot{G}_s} h(g_s, \dot{g}_s) w(g_s, \dot{g}_s)}{\Sigma_{G_s} \Sigma_{\dot{G}_s} w(g_s, \dot{g}_s)} \quad (16)$$

where r is the current risk metric, $$w(g_s, \dot{g}_s) = \exp\left(-\frac{1}{2}[g_s - g \quad \dot{g}_s - \dot{g}]P_g^{-1}\begin{bmatrix} g_s - g \\ \dot{g}_s - \dot{g} \end{bmatrix}\right), \quad (17)$$

$G_s$ is the distribution of glucose values and $\dot{G}_s$ is the distribution of glucose rates of change determined from the glucose state distribution around the detected glucose state, $h(g_s, \dot{g}_s)$ is the cumulative hazard value of the return path at each glucose state, g is the glucose value for the current risk metric, $\dot{g}$ is the rate of change of the glucose level for the current risk metric, $$P_g = \begin{bmatrix} \sigma_g^2 & \sigma_g \sigma_{\dot{g}} \\ \sigma_{\dot{g}} \sigma_g & \sigma_{\dot{g}}^2 \end{bmatrix}. \quad (18)$$

$\sigma_g$ is the standard deviation of g, and $\sigma_{\dot{g}}$ is the standard deviation of $\dot{g}$. The weighting of the cumulative hazard values results in samples closest to the measured glucose state receiving the largest weight in the final current risk metric calculation.

Figure 8A:
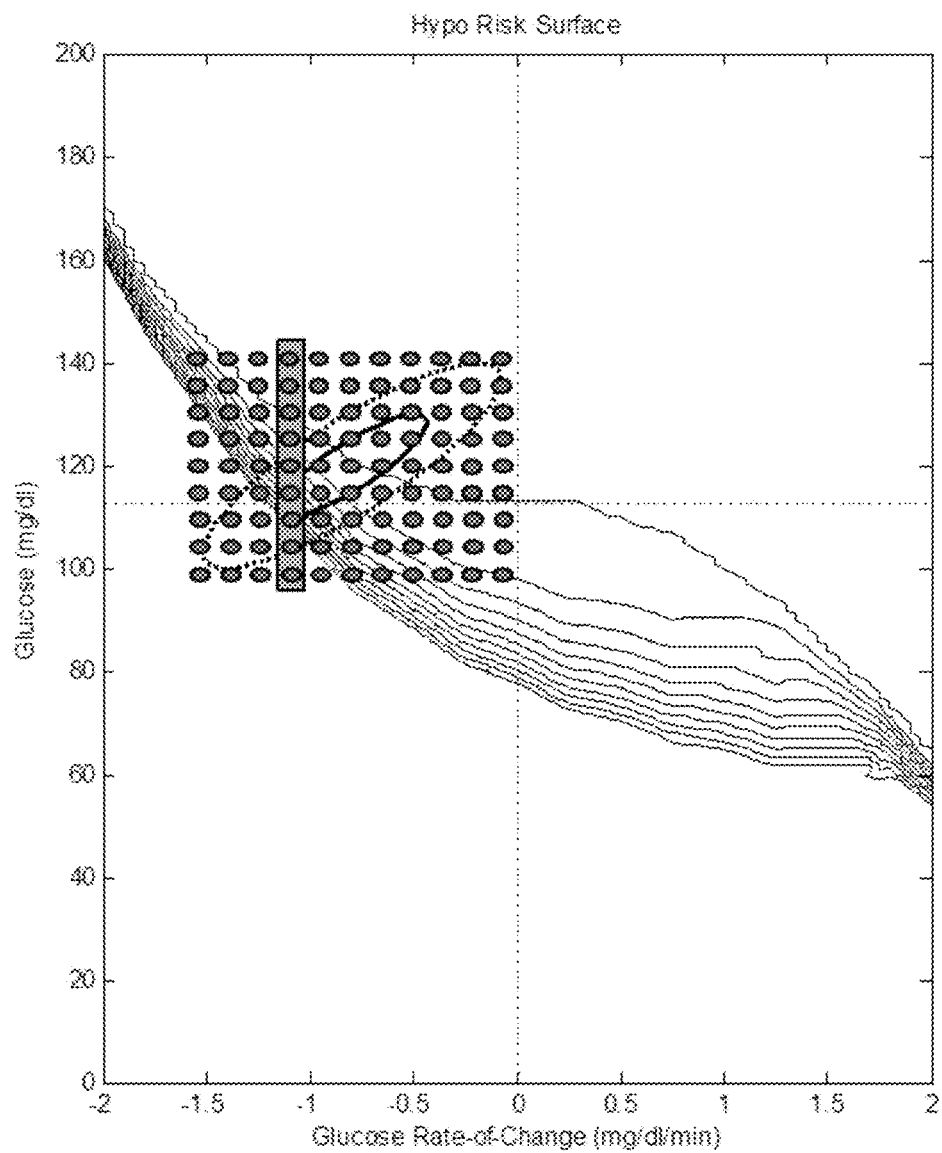
FIG. 8A illustrates a hypoglycemic risk surface with an array of samples positions corresponding to a glucose state distribution.
Figure 8B:
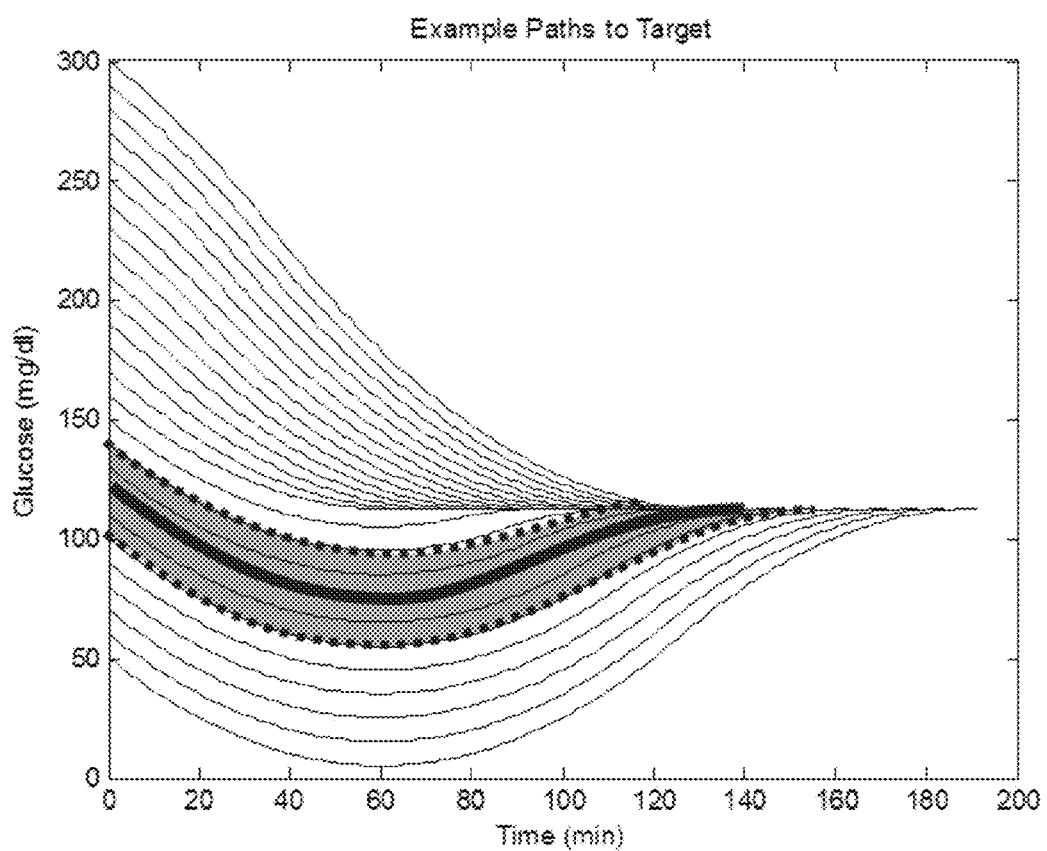
FIG. 8B illustrates exemplary return paths for the highlighted glucose states of FIG. 8A.

With reference to FIGS. 8A and 8B, determination of the current risk metric is visually displayed. FIG. 8A illustrates the 99 glucose states generated in an 11×9 matrix when k=10 and n=8 overlaid onto a hypoglycemic risk surface. The return paths for the 9 highlighted samples from FIG. 8A are also highlighted in FIG. 8B. The weighted average of the cumulative hazard values for the return paths for the entire grouping of the 99 glucose states provides the current risk metric.

The final basal multiplier for each CTR period is determined utilizing the current risk metric. The current risk metric is first converted to a basal multiplier value between 0 and $TBR_{MAX}$. $TBR_{MAX}$ is the maximum percentage for a temporary basal rate (TBR). In at least one embodiment, the $TBR_{MAX}$ defaults to 250%. In further embodiments, the $TBR_{MAX}$ is lower or higher than 250% and is adjusted to tune the control and determination for hypo-adverse individuals. The basal multiplier value is defined by the following equation:

$$BM(r) = \begin{cases} \frac{r - r_{0\%}}{-r_{0\%}}, & r > r_{0\%} \\ 0, & r \le r_{0\%} \end{cases} \quad (19)$$

where BM(r) is the basal multiplier value, r is the current risk metric, and $r_{0\%}$ is a reference risk metric. In one or more embodiments, the reference risk metric is a glucose state linked to complete basal shutoff. For example, complete basal shutoff may occur at 70 mg/dl such that when the blood glucose level is below 70 mg/dl no basal insulin is provided. The basal multiplier value may be provided as a continuous function as the current risk metric varies. However, before providing the adjusted basal rate to the therapy delivery device 31 it is converted to the nearest TBR increment ($TBR_{inc}$) to provide an incremental basal rate multiplier ($BM_{inc}$). The incremental basal rate multiplier is defined by the following equation:

$$BM_{inc} = \min\left(\max\left(\text{floor}\left(\frac{BM(r)}{TBR_{inc}}\right)TBR_{inc}, 0\right), TBR_{MAX}\right). \quad (20)$$

Figure 9:
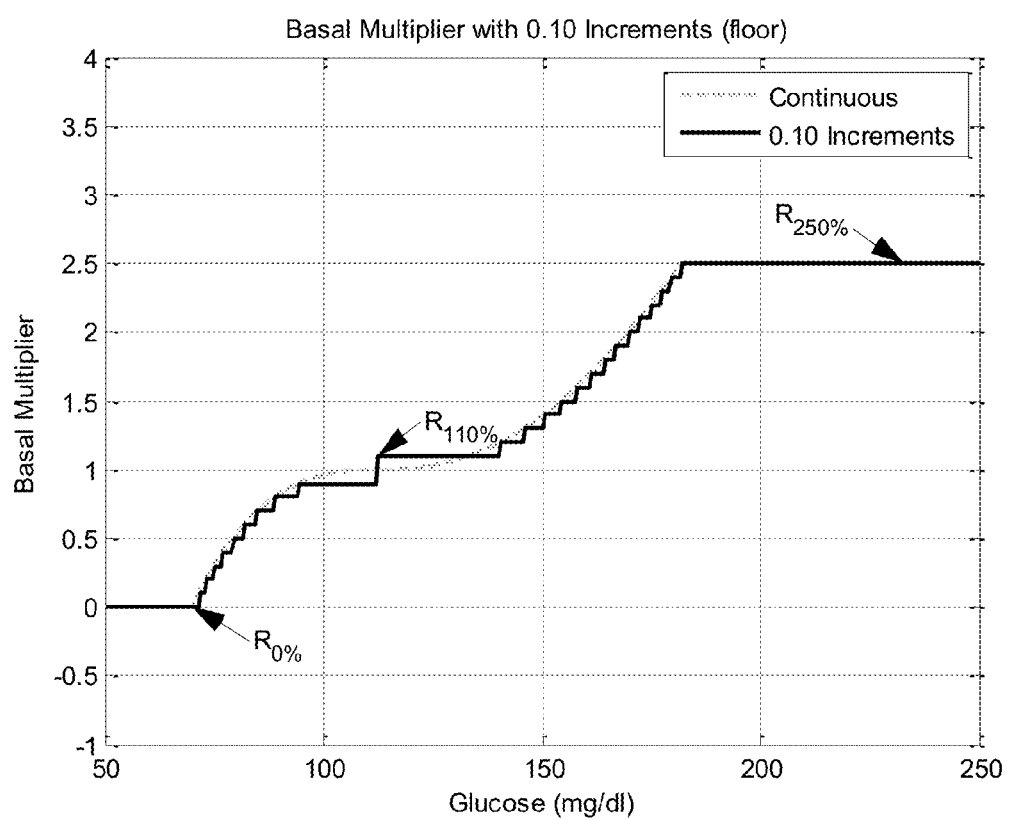
FIG. 9 illustrates a graph providing a continuous basal multiplier and an incremental basal multiplier.

With reference to FIG. 9, exemplary continuous basal multiplier values and incremental basal rate multipliers with a $TBR_{inc}$ of 10% and the implemented floor function are illustrated.

In another embodiment, basal multipliers greater than a threshold ($BM_{bolus}$) are delivered as a single bolus. The threshold could be 100%, 110%, or 130%. In these cases the extra insulin ($I_{TBR}$) that would be delivered in the next period of d minutes is calculated using the anticipated basal rate ($I_{BasalRate}$) for the period and the duration of the period (d). The extra insulin is then delivered as a single bolus and the basal rate multiplier is set to the threshold ($BM_{bolus}$).

$$I_{TBR} = (BM_{inc} - BM_{bolus}) I_{BasalRate} \frac{d}{60} \quad (21)$$

Figure 10A:
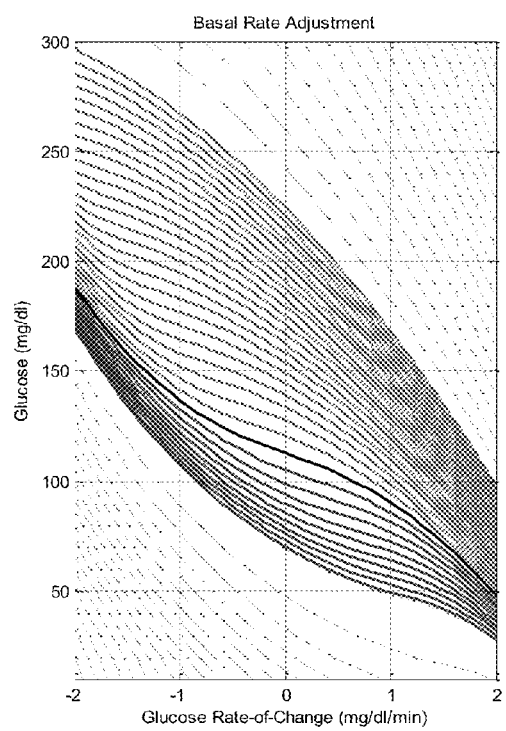
FIG. 10A illustrates a basal rate adjustment plot.
Figure 10B:
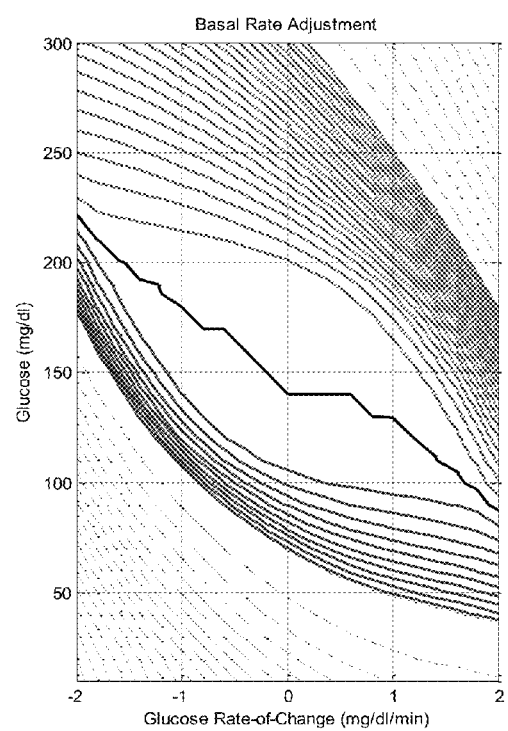
FIG. 10B illustrates a basal rate adjustment plot of FIG. 10A with a hyperglycemic shift due to a recent meal or correction bolus.

As previously discussed, if the PwD has had a recent meal or correction bolus, then a shift is applied to the hyperglycemic side of the hazard function 80. This reduces the calculated hyperglycemic risk since there is insulin in the subcutaneous compartment to account for a portion of the hyperglycemic risk. With reference to FIGS. 10A and 10B, the resulting shift in the basal rate adjustment from the initial shift applied to the hyperglycemic side of the hazard function 80 is illustrated. FIG. 10A provides an exemplary basal rate adjustment profile with the curve passing through a glucose of approximately 115 mg/dl and a rate-of-change of 0 mg/dl/min dividing basal rates above and below 100%; the curves below are basal rates below 100% and the curves above are basal rates above 100%. Similarly, FIG. 10B provides an exemplary basal rate adjustment profile with the hyperglycemic shift added. The lone curve passing through a glucose of approximately 140 mg/dl and a rate-of-change of 0 mg/dl/min divides basal rates above and below 100%.

For some PwDs the max allowed TBR ($TBR_{MAX}$) should be set to a value lower than 250% or the default setting for $TBR_{MAX}$. These individuals are characterized by having a large glucose correction equivalent of their basal rate ($G_{br}$). This is calculated by multiplying the hourly basal rate (BR) by the insulin sensitivity (IS). For example an individual with a nominal basal rate of 0.9 IU/hr and an insulin sensitivity of 50 mg/dl/IU would have a glucose correction equivalent of 45 mg/dl. PwD with a $G_{br}$ above a threshold ($G_{brT}$) could benefit from a lowered $TBR_{MAX}$. In one or more embodiments, the $G_{brT}$ is set at 150 mg/dl. It will be appreciated that the $G_{brT}$ may be set at values above or below 150 mg/dl as specific PwD circumstances warrant. A temporary basal rate limit ($TBR_{limit}$) to provide a reduced $TBR_{MAX}$ is defined by the following equation:

$$TBR_{limit} = \min\left(TBR_{MAX}, \frac{G_{brT}}{BR * IS} * TBR_{MAX}\right). \quad (22)$$

Similarly to the incremental basal rate multiplier, the temporary basal rate limit may be incremented to the closest TBR increment. The $TBR_{limit}$ is incremented to the closest TBR increment as defined by the following equation:

$$TBR_{inc\,limit} = \min\left(\max\left(\text{round}\left(\frac{TBR_{limit}}{10}\right) * TBR_{inc}, 100\right), 250\right). \quad (23)$$

The glucose correction equivalent was calculated for 30 simulated PwDs. The simulated subjects numbered 21 and 24 showed an oscillating behavior when their insulin sensitivity was increased. In this scenario the basal rate was increased by a factor of 1.5 for subject number 24 to induce hypoglycemia and the CTR algorithm was turned on to mitigate the effects. Simulations were repeated with different values for the max allowed TBR value ranging from 125% to 250%. The lower values for the max allowed TBR value have a lower magnitude of the oscillations demonstrating the benefit of implementing a $TBR_{limit}$ for PwD with a $G_{br}$ above the $G_{brT}$.

For further and alternative descriptions for determining the basal rate adjustment, see U.S. patent application Ser. No. 14/229,016, filed on Mar. 28, 2015, entitled "System and Method for Adjusting Therapy Based on Risk Associated with a Glucose State," the entire disclosure of which is incorporated by reference herein. For further description of calculating the target return paths and calculating risk metrics, see U.S. patent application Ser. No. 13/645,198, filed on Oct. 4, 2012, entitled "System and Method for Assessing Risk Associated with a Glucose State," the entire disclosure of which is incorporated by reference herein. For further description of the probability analysis tool, the recursive filter, the uncertainty calculation, and other probability and risk analysis functionalities of computing device 66, see U.S. patent application Ser. No. 12/693,701, filed on Jan. 26, 2010, entitled "Methods and Systems for Processing Glucose Data Measured from a Person Having Diabetes," and U.S. patent application Ser. No. 12/818,795, filed on Jun. 18, 2010, entitled "Insulin Optimization Systems and Testing Methods with Adjusted Exit Criterion Accounting for System Noise Associated with Biomarkers," the entire disclosures of which are incorporated by reference herein. For further description of the bolus calculator module 88, see U.S. patent application Ser. No. 13/593,557, filed on Aug. 24, 2012, entitled "Handheld Diabetes Management Device with Bolus Calculator," and U.S. patent application Ser. No. 13/593,575, filed on Aug. 24, 2012, entitled "Insulin Pump and Methods for Operating the Insulin Pump," the entire disclosures of which are incorporated by reference herein.

It should now be understood that the methods and systems described herein may be used to estimate the glucose level of a person having diabetes and utilize a control-to-range algorithm to adjust the glucose level of a person having diabetes. Furthermore, the methods and systems described herein may also be used to determine adjustments to the basal rate of insulin administration to the PwD. The methods described herein may be stored on a computer-readable medium which has computer-executable instructions for performing the methods. Such computer-readable media may include compact discs, hard drives, thumb drives, random-access memory, dynamic random-access memory, flash memory, and so forth.

It is noted that recitations herein of a component of the present disclosure being "configured" in a particular way, "configured" to embody a particular property, or function in a particular manner, are structural recitations, as opposed to recitations of intended use. More specifically, the references herein to the manner in which a component is "configured" denotes an existing physical condition of the component and, as such, is to be taken as a definite recitation of the structural characteristics of the component.

While particular embodiments and aspects of the present invention have been illustrated and described herein, various other changes and modifications may be made without departing from the spirit and scope of the invention. Moreover, although various inventive aspects have been described herein, such aspects need not be utilized in combination. It is therefore intended that the appended claims cover all such changes and modifications that are within the scope of this invention.

What is claimed is:

1. A method of determining and administering a basal rate adjustment of insulin based on risk associated with a glucose state of a person with diabetes, the method comprising:
   receiving, by at least one computing device, a signal representative of at least one glucose measurement;
   detecting, by the at least one computing device, a glucose state of the person based on the signal, the detected glucose state including a glucose level of the person and a rate of change of the glucose level;
   determining, by the at least one computing device, a current risk metric associated with the detected glucose state based on a target glucose state, the target glucose state being stored in memory accessible by the at least one computing device, the current risk metric indicating a risk of at least one of a hypoglycemic condition and a hyperglycemic condition of the person,
   wherein a return path is determined based on a transition from the current glucose state to the target glucose state, the return path comprising at least one intermediate glucose value associated with a return to the target glucose state,
   wherein a cumulative hazard value of the return path is determined, the cumulative hazard value including a sum of the hazard values of the at least one glucose value on the return path, each hazard value being indicative of a hazard associated with the corresponding intermediate glucose value,
   wherein the current risk metric is determined based on a weighted average of cumulative hazard values of return paths generated from a glucose state distribution around the detected glucose state;
   identifying, by the at least one computing device, a reference glucose state and a reference risk metric associated with the reference glucose state;
   calculating, by the at least one computing device, an adjustment to a basal rate of a therapy delivery device based on the current risk metric associated with the detected glucose state and the reference risk metric associated with the reference glucose level;
   transmitting a control signal to instruct the therapy delivery device to adjust the basal rate based on the calculated adjustment; and
   administering the adjusted basal rate to the person with diabetes.

2. The method of claim 1, wherein the calculating comprises mapping the current risk metric to a percent reduction of the basal rate based on the reference risk metric.

3. The method of claim 2, wherein the reference glucose state includes a glucose level corresponding to a hypoglycemic condition.

4. The method of claim 1, further comprising displaying to a user, on a graphical user interface, graphical data representative of the calculated adjustment to the basal rate.

5. The method of claim 1, wherein the therapy delivery device includes an insulin pump for delivering insulin to the person with diabetes, and the therapy delivery device is in communication with the at least one computing device for receiving the calculated adjustment of the basal rate.

6. The method of claim 1, wherein the hazard value for each of the hazard values of the at least one glucose value on the return path is determined by the at least one computing device in accordance with $$h(g)_{hyper} = \max(\alpha_{hyper} \cdot \alpha(\log(\max(g - \Delta g_{hyper} - \max(\Delta g_{hypo}, 0), 1))^c - \beta), 0),$$

$$h(g)_{hypo} = \min(\alpha(\log(\max(g - \Delta g_{hypo}, 1))^c - \beta), 0), \text{ and}$$

$$h(g) = \begin{cases} h_{MAX} & \text{if } g - \Delta g_{hyper} - \max(\Delta g_{hypo}, 0) \geq g_{MAX} \\ h_{MIN} & \text{if } g - \Delta g_{hypo} \leq g_{MIN} \\ h(g)_{hyper} & \text{if } h(g)_{hypo} \geq 0 \\ h(g)_{hypo} & \text{if } h(g)_{hypo} < 0 \end{cases}$$

where g is the glucose value, $\Delta g_{hyper}$ is a hyperglycemic shift, $\Delta g_{hypo}$ is a hypoglycemic shift, $h_{MAX}$ is a maximum hazard, $g_{MAX}$ is a glucose value above which no additional incremental hazard is calculated above $h_{MAX}$, $h_{MIN}$ is a minimum hazard, $g_{MIN}$ is a glucose value below which no additional incremental hazard is calculated above $h_{MIN}$, $\alpha_{hyper}$ is the hyperglycemic control aggressiveness, and $\alpha$, $\beta$, and c are process variables.

7. The method of claim 1, further comprising, prior to determining the cumulative hazard value of the return path, identifying, by the at least one computing device, a shifted glucose target for the person to account for a positively shifted hypoglycemic risk in accordance with $$\hat{g}_t = g_t + \max(\Delta g_{hypo}, 0)$$

where $\hat{g}_t$ is the shifted glucose target, $g_t$ is a nominal glucose target, and $\Delta g_{hypo}$ is a hypoglycemic shift.

8. The method of claim 7, wherein, if $T^{\pm} = t_1^{\pm} + t_2^{\pm}$ is a real number, the cumulative hazard value of the return path is determined by the at least one computing device according to $$h(g, \dot{g}) = \sum_{t=0}^{t_1^{\pm}} h\left(g + \dot{g}t + \frac{1}{2}\ddot{g}_p t^2\right) + \sum_{t=0}^{t_2^{\pm}} h\left(\hat{g}_t + \frac{1}{2}\ddot{g}_n t^2\right)$$

where $$t_1^{\pm} = \frac{\sqrt{\ddot{g}_n(\ddot{g}_p - \ddot{g}_n)(-\dot{g}^2 + 2\ddot{g}_p - 2\hat{g}_t\ddot{g}_p)} - \dot{g}\ddot{g}_p + \dot{g}\ddot{g}_n}{\ddot{g}_p(\ddot{g}_p - \ddot{g}_n)},$$

$$t_2^{\pm} = \frac{\dot{g} + \ddot{g}_p t_1^{\pm}}{-\ddot{g}_n},$$

$\dot{g}$ is the rate of change of the glucose level, $\ddot{g}_p$ is the maximum positive glucose acceleration, and $\ddot{g}_n$ is the maximum negative glucose acceleration.

9. The method of claim 7, wherein, if $T^{\mp} = t_1^{\mp} + t_2^{\mp}$ is a real number, the cumulative hazard value of the return path is determined by the at least one computing device according to $$h(g, \dot{g}) = \sum_{t=0}^{t_1^{\mp}} h\left(g + \dot{g}t + \frac{1}{2}\ddot{g}_n t^2\right) + \sum_{t=0}^{t_2^{\mp}} h\left(\hat{g}_t + \frac{1}{2}\ddot{g}_p t^2\right)$$

where $$t_1^{\mp} = \frac{\sqrt{\ddot{g}_p(\ddot{g}_n - \ddot{g}_p)(-\dot{g}^2 + 2\ddot{g}_n - 2\hat{g}_t\ddot{g}_n)} - \dot{g}\ddot{g}_n + \dot{g}\ddot{g}_p}{\ddot{g}_n(\ddot{g}_n - \ddot{g}_p)},$$

$$t_2^{\mp} = \frac{\dot{g} + \ddot{g}_n t_1^{\mp}}{-\ddot{g}_p},$$

$\dot{g}$ is the rate of change of the glucose level, $\ddot{g}_p$ is the maximum positive glucose acceleration, and $\ddot{g}_n$ is the maximum negative glucose acceleration.

10. The method of claim 1, wherein the glucose state distribution is determined by the at least one computing device according to $$G_s = \left[g - 2\sigma_g, g - 2\sigma_g + \frac{4\sigma_g}{k}, g - 2\sigma_g + 2\frac{4\sigma_g}{k}, \right.$$

$$g - 2\sigma_g + 3\frac{4\sigma_g}{k}, \ldots, g - 2\sigma_g + k\frac{4\sigma_g}{k}\right] \text{ and}$$

$$\dot{G}_s = \left[\dot{g} - 2\sigma_{\dot{g}}, \dot{g} - 2\sigma_{\dot{g}} + \frac{4\sigma_{\dot{g}}}{n}, \dot{g} - 2\sigma_{\dot{g}} + 2\frac{4\sigma_{\dot{g}}}{n},\right.$$

$$\left.\dot{g} - 2\sigma_{\dot{g}} + 3\frac{4\sigma_{\dot{g}}}{n}, \ldots, \dot{g} - 2\sigma_{\dot{g}} + n\frac{4\sigma_{\dot{g}}}{n}\right]$$

where $G_s$ is the distribution of glucose values, $\dot{G}_s$ is the distribution of glucose rates of change, g is the glucose value for the current risk metric, $\dot{g}$ is the rate of change of the glucose level for the current risk metric, $\sigma_g$ is the standard deviation of g, $\sigma_{\dot{g}}$ is the standard deviation of $\dot{g}$, k is the number of divisions of $G_s$, and n is the number of divisions of $\dot{G}_s$.

11. The method of claim 10, wherein k=10 and n=8.

12. The method of claim 1, wherein the current risk metric is determined by the at least one computing device according to $$r = \frac{\Sigma_{G_s}\Sigma_{\dot{G}_s} h(g_s, \dot{g}_s) w(g_s, \dot{g}_s)}{\Sigma_{G_s}\Sigma_{\dot{G}_s} w(g_s, \dot{g}_s)}$$

where r is the current risk metric, $$w(g_s, \dot{g}_s) = \exp\left(-\frac{1}{2}[g_s - g \quad \dot{g}_s - \dot{g}]P_g^{-1}\begin{bmatrix} g_s - g \\ \dot{g}_s - \dot{g} \end{bmatrix}\right),$$

$G_s$ is the distribution of glucose values and $\dot{G}_s$ is the distribution of glucose rates of change determined from the glucose state distribution around the detected glucose state, $h(g_s, \dot{g}_s)$ is the cumulative hazard value of the return path at each glucose state, g is the glucose value for the current risk metric, $\dot{g}$ is the rate of change of the glucose level for the current risk metric, $$P_g = \begin{bmatrix} \sigma_g^2 & \sigma_g \sigma_{\dot{g}} \\ \sigma_{\dot{g}} \sigma_g & \sigma_{\dot{g}}^2 \end{bmatrix},$$

$\sigma_g$ is the standard deviation of g, and $\sigma_{\dot{g}}$ is the standard deviation of $\dot{g}$.

13. The method of claim 2, wherein a basal multiplier value is determined by the by the at least one computing device according to $$BM(r) = \begin{cases} \frac{r - r_{0\%}}{-r_{0\%}}, & r > r_{0\%} \\ 0, & r \leq r_{0\%} \end{cases}$$

where BM(r) is the basal multiplier value, r is the current risk metric, and $r_{0\%}$ is the reference risk metric.

14. The method of claim 13, wherein $r_{0\%}$ is the risk metric at a glucose state linked to complete basal shutoff.

15. The method of claim 14, wherein a temporary basal rate is determined for transmission to the therapy delivery device is determined by the at least one computing device according to $$BM_{inc} = \min\left(\max\left(\text{floor}\left(\frac{BM(r)}{TBR_{inc}}\right)TBR_{inc}, 0\right)TBR_{MAX}\right)$$

where $TBR_{inc}$ is the sizing of a temporary basal rate multiplier adjustment increment and $TBR_{MAX}$ is the maximum temporary basal rate multiplier.

16. The method of claim 15, wherein a temporary basal rate multiplier limit accounting for insulin sensitivity of the person is determined by the at least one computing device according to $$TBR_{limit} = \min\left(TBR_{MAX}, \frac{G_{brT}}{BR*IS} * TBR_{MAX}\right)$$

where $TBR_{limit}$ is the temporary basal rate multiplier limit, $G_{brT}$ is a glucose correction equivalent threshold, BR is the nominal basal rate, and IS is the insulin sensitivity of the person.

17. The method of claim 16, wherein the $TBR_{MAX}$ is 250% and the $G_{brT}$ is 150 mg/dl.

18. The method of claim 6, wherein $\Delta g_{hyper}$ and $\Delta g_{hypo}$ are adjusted based on detection of an over-correction bolus.

19. A blood glucose management device configured to determine a basal rate adjustment based on risk associated with a glucose state of a person with diabetes, the device comprising: a non-transitory computer-readable medium storing executable instructions;

and at least one processing device configured to execute the executable instructions such that, when executed by the at least one processing device, the executable instructions cause the at least one processing device to:
receive a signal representative of at least one glucose measurement;
detect a glucose state of the person based on the signal, the detected glucose state including a glucose level of the person and a rate of change of the glucose level;
determine a current risk metric associated with the detected glucose state based on a target glucose state, the target glucose state being stored in memory accessible by the at least one computing device, the current risk metric indicating a risk of at least one of a hypoglycemic condition and a hyperglycemic condition of the person,
wherein a return path is determined based on a transition from the current glucose state to the target glucose state, the return path comprising at least one intermediate glucose value associated with a return to the target glucose state,
wherein a cumulative hazard value of the return path is determined, the cumulative hazard value including a sum of the hazard values of the at least one glucose value on the return path, each hazard value being indicative of a hazard associated with the corresponding intermediate glucose value,
wherein the current risk metric is determined based on a weighted average of cumulative hazard values of return paths generated from a glucose state distribution around the detected glucose state;
identify a reference glucose state and a reference risk metric associated with the reference glucose state;
calculate an adjustment to a basal rate of a therapy delivery device based on the current risk metric associated with the detected glucose state and the reference risk metric associated with the reference glucose level;
transmit a control signal to instruct the therapy delivery device to adjust the basal rate based on the calculated adjustment; and
administer the adjusted basal rate to the person with diabetes.

* * * * *

UNITED STATES PATENT AND TRADEMARK OFFICE
CERTIFICATE OF CORRECTION

PATENT NO.        : 10,297,350 B2
APPLICATION NO.   : 15/170468
DATED             : May 21, 2019
INVENTOR(S)       : David L. Duke et al.

Page 1 of 1

It is certified that error appears in the above-identified patent and that said Letters Patent is hereby corrected as shown below:

On the Title Page

Page 2, Column 2, item [56], Line 53 Cite No. 18, after "transplantation", delete "fo" and insert --for--, therefor.

Signed and Sealed this
Twenty-sixth Day of November, 2019

Andrei Iancu
*Director of the United States Patent and Trademark Office*